United States Patent
Lefebvre

(10) Patent No.: US 7,317,818 B2
(45) Date of Patent: Jan. 8, 2008

(54) METHOD OF ENABLING AN ANALYSIS OF AN EXTERNAL BODY PORTION

(75) Inventor: Marc-André Lefebvre, Coulombiers (FR)

(73) Assignee: L'Oréal S.A., Paris (FR)

( * ) Notice: Subject to any disclaimer, the term of this patent is extended or adjusted under 35 U.S.C. 154(b) by 1371 days.

(21) Appl. No.: 09/991,913

(22) Filed: Nov. 26, 2001

(65) Prior Publication Data

US 2003/0099383 A1 May 29, 2003

(51) Int. Cl.
*G06K 9/00* (2006.01)
(52) U.S. Cl. .................... 382/128; 128/889
(58) Field of Classification Search ............... 128/889; 132/200; 604/23; 514/2, 17; 382/128; 600/438, 600/587; 424/9.1, 9.34; 435/4, 174, 177
See application file for complete search history.

(56) References Cited

U.S. PATENT DOCUMENTS

| | | | |
|---|---|---|---|
| 3,976,066 A * | 8/1976 | McCartney | 128/889 |
| 5,555,900 A * | 9/1996 | Rich | 132/200 |
| 5,636,637 A | 6/1997 | Guiolet et al. | 600/476 |
| 5,640,957 A | 6/1997 | Kaminski et al. | 600/407 |
| 6,179,804 B1 * | 1/2001 | Satterfield | 604/23 |
| 6,444,647 B1 * | 9/2002 | Robinson et al. | 514/17 |
| 6,492,326 B1 * | 12/2002 | Robinson et al. | 514/2 |

FOREIGN PATENT DOCUMENTS

| | | |
|---|---|---|
| CH | 683 668 | 4/1994 |
| EP | 0 799 599 | 10/1997 |
| EP | 0 992 232 | 4/2000 |
| EP | 1 169 964 | 1/2002 |
| GB | 2 235 767 | 3/1991 |
| JP | 2001-163759 | 6/2001 |
| PL | 2001-108674 | 4/2001 |

\* cited by examiner

*Primary Examiner*—Anh Hong Do
(74) *Attorney, Agent, or Firm*—Finnegan, Henderson, Farabow, Garrett & Dunner, L.L.P.

(57) ABSTRACT

A method of enabling an analysis taking into account exposure of at least one external body portion to the environment comprises obtaining first information representative of at least one condition of a first external body portion of a subject and obtaining second information representative of at least one condition of a second external body portion of the subject. The method further comprises determining a difference between the first information and the second information so as to enable an analysis taking into account impact of at least one environmental factor. The second external body portion is normally less exposed to at least one environmental factor than the first external body portion.

131 Claims, 13 Drawing Sheets

METHOD OF ENABLING AN ANALYSIS OF AN EXTERNAL BODY PORTION

FIELD OF THE INVENTION

The present invention relates to a method of enabling an analysis taking into account exposure of at least one external body portion to the environment. In one example, the invention may be used to determine the effects of environmental factors on the skin, hair, and/or nails. One other aspect of the invention relates to a method of enabling a determination of at least the initial effectiveness of a treatment for an external body portion.

DESCRIPTION OF THE RELATED ART

People use a wide range of beauty products to enhance their physical appearance. In one example, cosmetic products are applied to the skin for rectification and prevention of damage caused by factors such as stress, aging, and the environment. These cosmetic products are selected based on their ability to treat particular types of skin conditions. To select the proper cosmetic products for a particular person, one must assess the person's skin and identify the types of rectification and prevention that are needed.

Conventional techniques for assessing skin, however, often do not provide an accurate representation of an individual's skin condition. Some of these techniques rely on comparisons between a person's skin and the skin of an average person of the same age. Where the person's skin is different from that of the average person at her age, inappropriate cosmetic products may be selected for her.

Other conventional skin assessment techniques involve comparisons between a person's skin and the ideal skin of a much younger person, such as a model. In one such technique, an image of the person's face is compared with an image of the model's face to aid in the selection of products for rectification and prevention. Because the attributes of the model's skin are unattainable by the person, she may feel discouraged and dissatisfied with her appearance. Further, excessive quantities of a product or products of excessive strength may be recommended, even though such excess product quantities or strengths might not achieve a desired result.

One aspect of the invention provides a method of enabling an analysis taking into account exposure of at least one external body portion to the environment. The method may comprise obtaining first information representative of at least one condition of a first external body portion of a subject and obtaining second information representative of at least one condition of a second external body portion of the subject. The method may further comprise determining a difference between the first information and the second information so as to enable an analysis taking into account impact of the at least one environmental factor. The second external body portion may be normally less exposed to at least one environmental factor than the first external body portion.

In another aspect, the first information may be representative of one or more conditions of the first external body portion of the subject at approximately a first time and the second information may be representative of one or more conditions of the second external body portion of the subject at approximately the first time. According to this aspect, the method may further comprise obtaining third information, which is representative of the one or more conditions of the first external body portion of the subject at approximately a second time, obtaining fourth information, which is representative of the one or more conditions of the second external body portion of the subject at approximately the second time, and determining a difference between the third information and the fourth information. The second time may occur at least a period of time after the first time.

In yet another aspect, the difference between the first information and the second information may be compared with the difference between the third information and the fourth information so as to enable an analysis taking into account impact of the one or more environmental factors over at least the period of time.

In a further aspect, a treatment may be selected for the first external body portion based on the difference between the first information and the second information.

In a still further aspect, there is a method of determining at least the initial effectiveness of a treatment. The method may comprise obtaining first information, which is representative of one or more conditions of a first external body portion of a subject at approximately a first time, obtaining second information, which is representative of one or more conditions of a second external body portion of the subject at approximately the first time, and determining a difference between the first information and the second information. The method may further comprise obtaining third information, which is representative of the one or more conditions of the first external body portion at approximately a second time, obtaining fourth information, which is representative of the one or more conditions of the second external body portion at approximately the second time, determining a difference between the third information and the fourth information, and comparing the difference between the first information and the second information with the difference between the third information and the fourth information. The second time may occur at least a period of time after a treatment of the first external body portion is initiated.

It is to be understood that both the foregoing general description and the following detailed description are exemplary and explanatory only and are not restrictive of the invention, as claimed.

The accompanying drawings, which are incorporated in and constitute a part of this specification, illustrate several exemplary embodiments of the invention and together with the description, serve to explain certain principles of the invention. In the drawings, FIG. 1 is an exemplary flowchart illustrating a method in accordance with an exemplary embodiment of the invention;

Reference will now be made in detail to exemplary embodiments of the invention, examples of which are illustrated in the accompanying drawings. Wherever possible, the same reference numbers will be used throughout the drawings to refer to the same or like parts.

One exemplary method of the invention enables an analysis taking into account exposure of one or more external body portions to the environment. Some examples of the method might relate to one or more external body portions that have received an application of a product, while other examples of the method might relate to situations where a product has not been applied.

Figure 1:
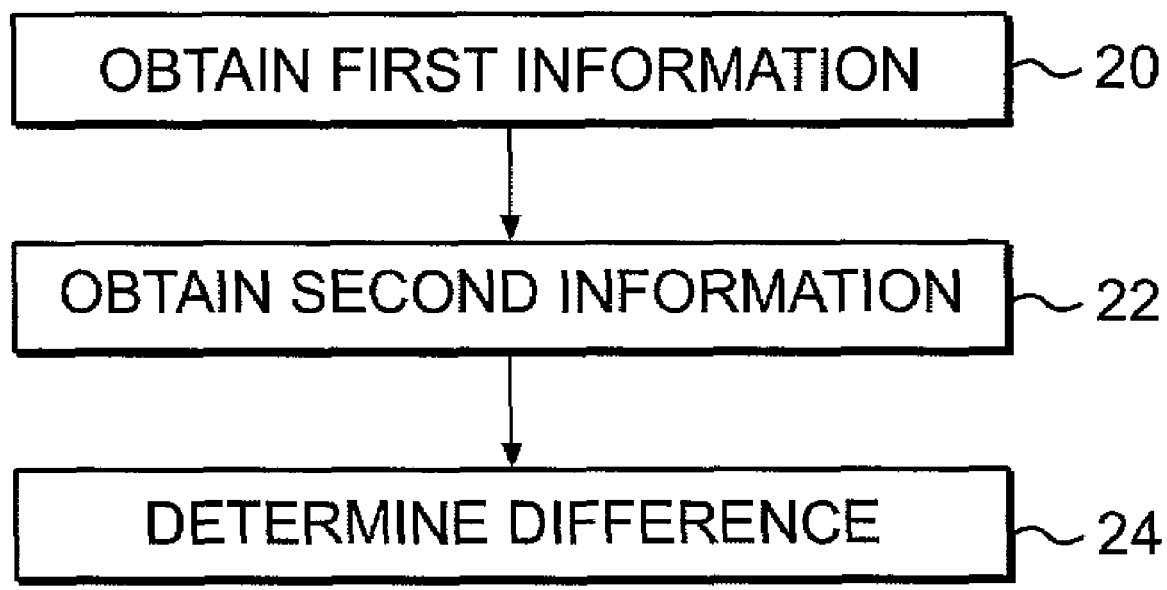

The flowchart in FIG. 1 illustrates one example of a method. As shown, the method may comprise obtaining first information representative of one or more conditions of a first external body portion of a subject (step 20), obtaining second information representative of one or more conditions of a second external body portion of the subject (step 22), and determining a difference between the first information and the second information (step 24). In this embodiment, the second external body portion may be normally less exposed to one or more environmental factors than the first external body portion. In other words, during the life of the subject, the second external body portion has been substantially less exposed to one or more environmental factors than the first external body portion. For example, the second external body portion could be normally covered with clothing and/or exposure to the environment could be blocked by another portion of the body. In another example, the second external body portion could be an area that is not normally shaved, while the first external body portion could be an area that is regularly shaved, such as the skin of the face or legs.

The one or more environmental factors may be ultraviolet radiation, extreme temperature, wind, pollution, and/or shaving, for example. Further, the one or more environmental factors may comprise a plurality of environmental factors.

Figure 2:
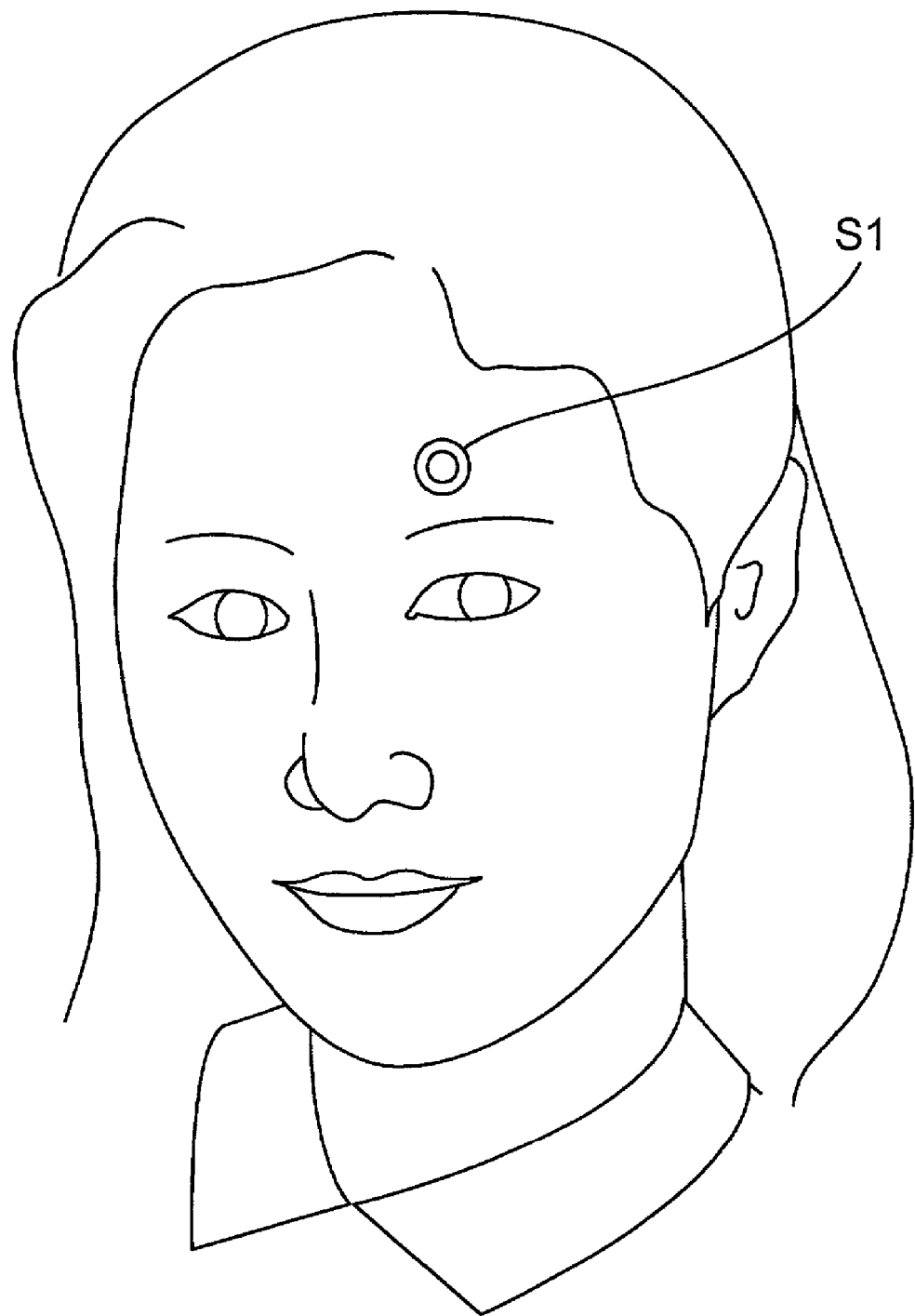
FIG. 2 is a schematic showing a first external body portion where information may be obtained according to an exemplary embodiment of the invention.

In one embodiment, the first external body portion of step 20 may comprise skin and/or hair located on parts of the body that are normally subjected to environmental factors. One example is a skin region located on the face of the subject, such as skin region S1 located on the forehead, as shown in FIG. 2. Information about one or more conditions of this external body portion may be obtained using any known acquisition device, as described below. In addition (or in the alternative) to obtaining information about one or more conditions of skin on the forehead, information may also be obtained about the condition(s) of other areas of the face, as well as other skin and/or hair regions normally exposed to environmental factors. As explained below, information may also be obtained about the condition(s) of fingernails and/or toenails.

The conditions of the external body portion may comprise texture, elasticity, dryness, cellulitis, sweating, aging, wrinkles, exfoliation, desquamation, homogeneity of color, micro-circulation, shininess, softness, smoothness, hydration, sebum production, cleanliness, irritation, redness, vasomotion, vasodilation, vasoconstriction, pigmentation, and/or freckles.

The second external body portion of step 22 may comprise skin, nails, and/or hair located on parts of the body that are not normally subjected to substantial environmental factors, as compared to the first external body portion. Examples include skin located on the upper buttocks of the subject, such as the skin region S2 shown in FIG. 3, and/or skin located on an inner surface of an upper part of at least one of the subject's arms, such as the skin region S2' shown in FIG. 4, for example.

Figure 3:
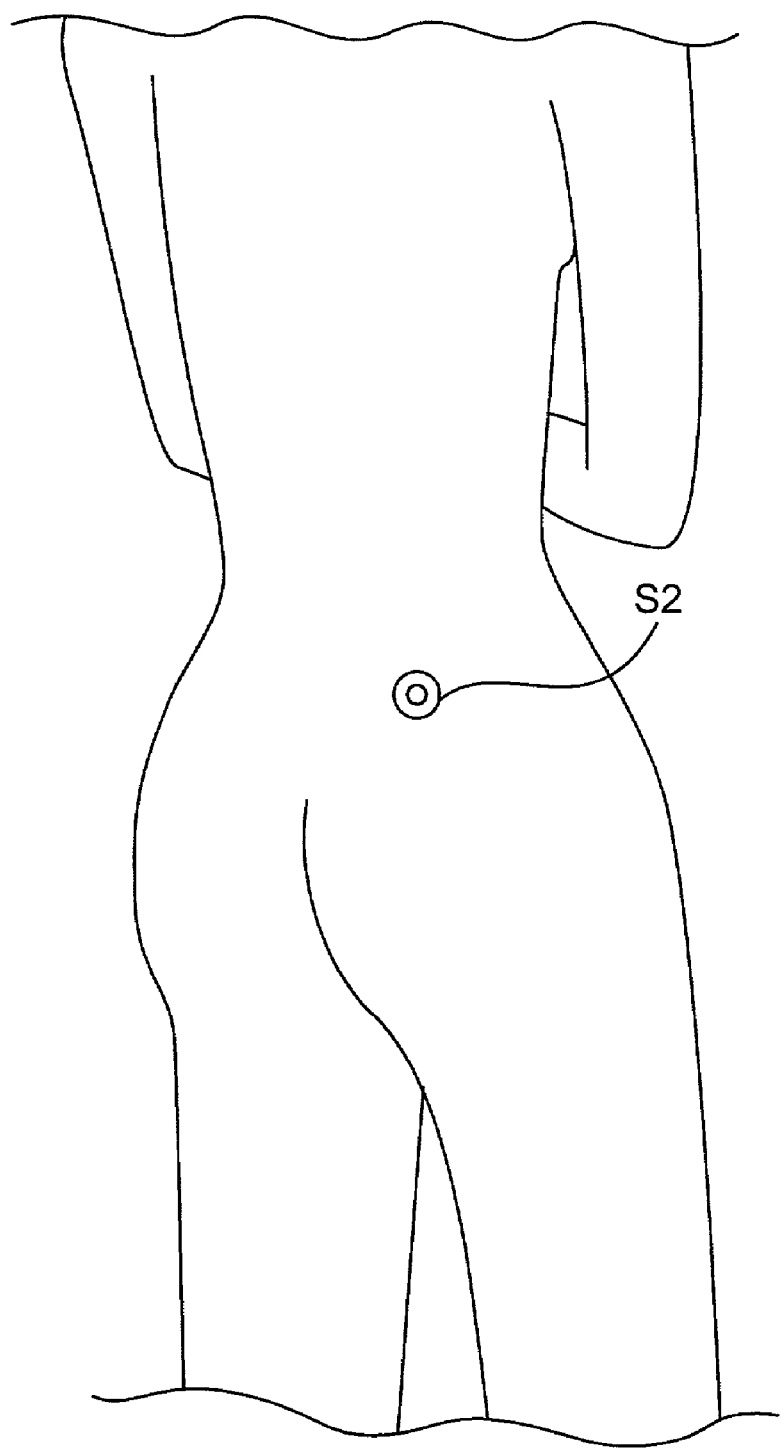
FIG. 3 is a schematic showing a second external body portion where information may be obtained according to an exemplary embodiment of the invention.

Although FIG. 3 shows one example of a skin region S2 located on the "upper buttocks," this skin region is not limited to the specific location shown in FIG. 3, and may include a skin region from any other location on the lower back and/or upper buttocks that is not normally subjected to substantial environmental factors. Likewise, information may be obtained from skin located on areas of the subject's arms other than skin region S2' shown in FIG. 4, as well as skin, nails, and/or hair from other body parts that are not normally subjected to substantial environmental factors.

Information about one or more conditions of the second external body portion may be obtained using any known acquisition device, as described below. For example, the same type of acquisition device could be used to obtain the information about the first and second portions.

The second external body portion may be subject to the same nutrition, hormones, and/or chronological aging as the first external body portion, and the second external body portion may be either substantially less exposed to environmental factors or substantially free from exposure to environmental factors, as compared to the first external body portion. Thus, a comparison of skin, nails, and/or hair from these two locations may isolate the effects of environmental factors on the first external body portion by eliminating effects based on nutritional factors, hormonal factors, and/or chronological aging factors.

Figure 4:
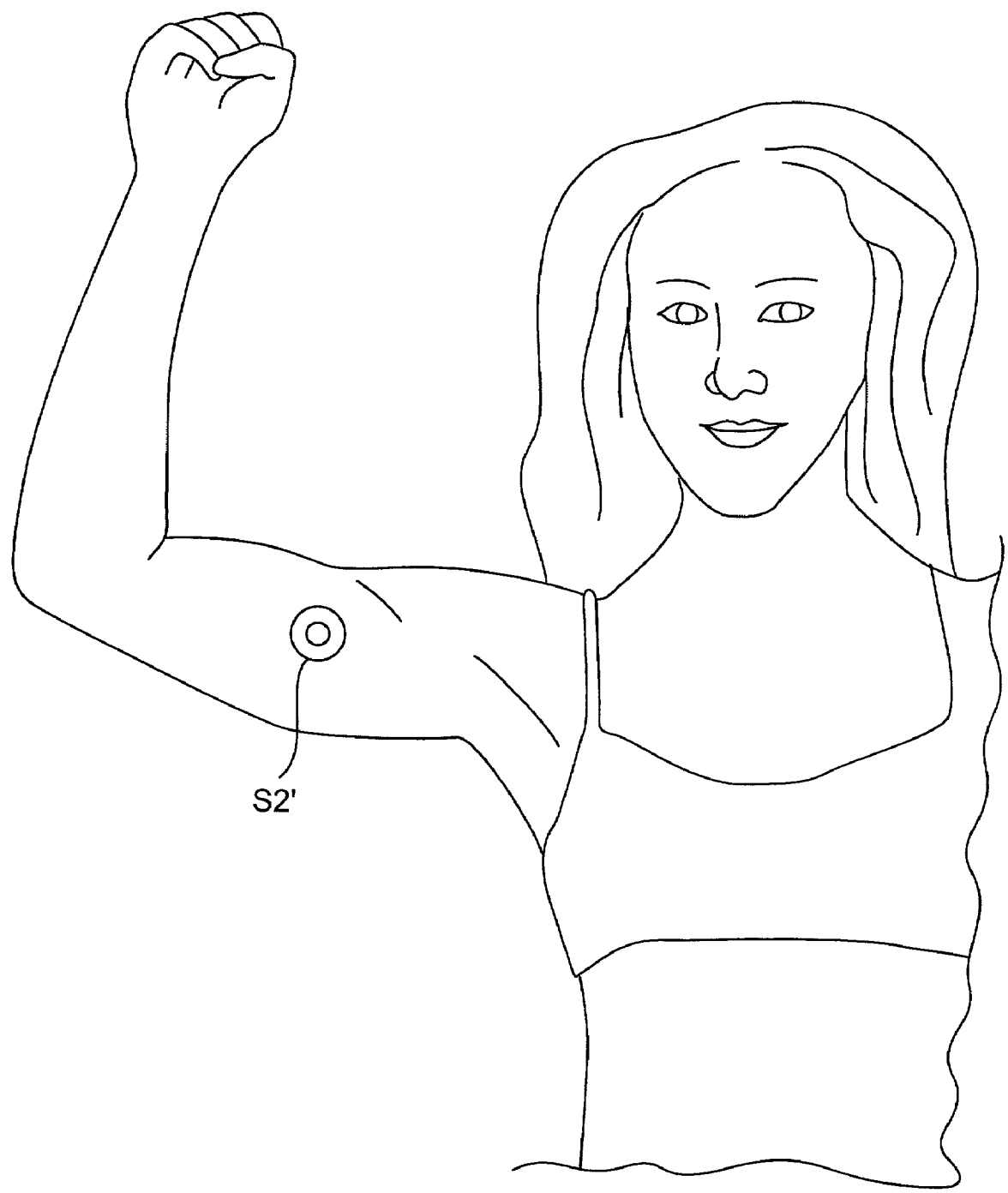
FIG. 4 is a schematic showing an alternative second external body portion.

Although FIG. 2, and FIGS. 3 and 4, respectively, show examples of areas of the body that might by considered as locations for the first and second body portions, there are many alternative locations that could be selected. For example, the first external body portion and the second external body portion may comprise hair or portions of hair on the subject's scalp. For example, the first external body portion may be hair or a portion of hair from an area that is normally exposed to environmental factors (e.g., free end portions of hair on a subject's scalp), whereas the second external body portion may be hair or a portion of hair that is normally not substantially exposed (e.g., root portions of hair on a subject's scalp). These portions may be more readily defined for subjects with longer hair and/or hair having a somewhat constant styling. In a further example, the first external body portion may comprise hair or portions thereof from the scalp and the second body portion may comprise hair or portions thereof from the armpit.

In another example, the first external body portion and the second external body portion may comprise different portions of a single hair, fingernail, and/or toenail. For example, the first external body portion may comprise a tip of a subject's fingernail and the second external body portion may comprise a root portion of the same fingernail.

Alternatively, the first external body portion may comprise a portion of a subject's fingernail and the second external body portion may comprise a portion of a subject's toenail.

In a further embodiment, the first external body portion may comprise hair and/or skin located on the scalp of the subject and the second external body portion may comprise hair and/or skin located in the pubic area of the subject.

It should be understood that although the method illustrated in FIG. 1, in its broadest sense, may include the obtaining of information for a pair of external body portions, the method may also include the obtaining of information for more than two external body portions.

Several exemplary embodiments of the invention will now be described with reference to FIG. 1.

According to one embodiment, each of the obtaining of the first information (step 20) and the obtaining of the second information (step 22) may comprise acquiring a quantitative measurement of one or more conditions. A quantitative measurement may also be acquired for each of a plurality of conditions.

The quantitative measurement may be chosen from any known quantitative measurement, such as corneometry, dermal torque measurement, pH measurement, colorimetry, sebumetry, lipometry, confocal measurement, epidermal turnover measurement, skin layer thickness measurement, blood microcirculation measurement, desquamation rate measurement, water loss measurement, skin hydration measurement, scoring with a densiscore-type tool, and measurement of sudatory function. An appropriate acquisition device may be used for each measurement. Examples include torque measuring devices, pH sensors, and other conventional devices that could be used to acquire information about the condition of skin, nails, and/or hair.

The quantitative measurement may be performed by the subject and/or by at least one provider. The provider may be a cosmetologist, a clinician, or other professional. Further, the measurement may be performed in the subject's home or at a location remote from the user's home, such as a kiosk, store, or the office of a cosmetologist or clinician.

In one example, a subject and/or provider may measure the pH of the skin on the subject's forehead and upper buttocks by pressing a conventional pH sensing device in place against the respective locations for a period of time. The pH sensing device may provide a numerical pH reading or may present the pH data as a color on a coded scale. One example of a pH sensing device includes a device configured to obtain data in a "kinetic approach" wherein a continuous measurement and/or a series of measurements is/are taken over a period of time to enable a plot of a pH curve over time. For example, such a kinetic device could be used to analyze liquid in contact with the skin, such as skin secretions.

In another example, a provider, such as a clinician or cosmetologist, may measure the elasticity of the skin on a subject's face and on an inner surface of an upper arm using a dermal torque measuring device.

There are numerous ways in which the difference between the first and second information could be determined in accordance with step 24 of FIG. 1. When the first and second information are in quantitative (e.g., numeric) forms, the determination might include a calculation, such as a subtraction, of one of the first and second information from the other. The calculation could be performed by one or more users, optionally with the assistance of a computer or any conventional calculation device, or by any type of device capable of making the calculation. For example, the device used to initially acquire the information might be configured to calculate the difference. In another example, information initially acquired by the device could be transferred to a computer (e.g., obtained by the computer) and the computer could make a determination of the difference. In another example, the difference could be determined by viewing one or more visual representations (e.g., graphical illustrations) of the conditions.

In certain circumstances (e.g., when the condition relates to a qualitative property), the condition of each external body portion could be "graded" to give the condition a quantitative value that could then be used in a calculation of the difference. In other circumstances where it might be difficult to assign a quantitative value for the condition of each external body location, the difference determination might comprise specifying a gradation of the difference between the conditions of the locations.

The determining of the difference between the first information and the second information (step 24) may comprise determining one or more differences between a quantitative measurement of the condition of the first external body portion and a quantitative measurement of the condition of the second external body portion. With reference to the above examples, a subject may determine the difference between the pH at each external body location by comparing the numerical pH values or pH color indications that were measured. Likewise, a provider may determine the difference between the elasticity of the skin at each external body location by comparing numerical readings provided by a dermal torque measuring device.

According to another embodiment of the method shown in the flowchart of FIG. 1, each of the obtaining of the first information (step 20) and the obtaining of the second information (step 22) may comprise acquiring at least one image of a respective external body portion of the subject. The at least one image may be chosen from photographs, scanned images, ultrasonic images, magnified images, wrinkle projections, and imprints. A plurality of images may be acquired.

The images may be acquired by the subject and/or by at least one provider in the subject's home or at a location remote from the subject's home.

In one example, a subject may photograph (e.g., with a film camera or digital camera) the skin on her face and photograph the skin on her upper buttocks. The subject may then transfer the photographs to a provider for analysis, described below. There are many different ways in which the photographs could be transferred. For example, the subject may deliver the photographs to the provider in person, send them using a package delivery service, such as a postal service or a courier, or send them electronically. To enable electronic transmission of the images, the subject may use a digital camera and/or an image scanner (e.g., a flat bed document scanner) to acquire the images of her skin and/or hair, then send the images using a computer network, for example by e-mail.

In another example, a provider may acquire ultrasound images and/or imprint images of the skin on the subject's face and the skin on her upper buttocks. The provider could analyze the images and/or send them to another provider for analysis. Again, the images may be delivered in person, sent using a postal or package delivery service, or sent electronically.

Each of the obtaining of the first information (step 20) and the obtaining of the second information (step 22) may further comprise analyzing one or more images to ascertain one or more qualitative properties and/or quantitative properties relating to the condition(s) of the external portion. A plurality of qualitative properties and quantitative properties may be ascertained from the analysis.

The analyzing of the images may comprise counting sebaceous glands, counting sweat glands, and/or visualizing imprints in the at least one image.

With reference to the above examples, a provider may analyze photographs by counting sebaceous glands, counting sweat glands, and/or identifying skin coloration. Also, the provider may analyze an ultrasound image and/or imprint image of the skin by counting sebaceous glands, counting sweat glands, and/or examining wrinkles.

The determining of the difference between the first information and the second information (step 24) may comprise determining at least one difference between one or more properties ascertained from analyzing an image of the first external body portion and one or more properties ascertained from analyzing an image of the second external body portion. For example, there could be a determination of the difference between the number of glands in the skin at each location, and/or the difference in coloration, and/or wrinkling of the skin at each location.

According to a further embodiment of the method shown in the flowchart of FIG. 1, each of the obtaining of the first information (step 20) and the obtaining of the second information (step 22) may comprise acquiring at least one external body portion sample. The at least one sample may be chosen from skin cells, hair cells, fingernail cells, toenail cells, secretions, bioanalytical content, bacteriological content, and enzymatic content. A plurality of samples may be acquired.

The acquiring of the at least one sample may be carried out using any known technique, including a technique using adhesive collection, absorption, and/or abrasion. An appropriate acquisition device may be used for each technique. For example, the sample collection could occur at the skin region SI of FIG. 1, at the skin region S2 of FIG. 2, and/or at the skin region S2' of FIG. 3.

In an adhesive collection technique, a support, such as a plastic strip, coated on one side with adhesive may be placed with its adhesive side in contact with a body portion, such as the skin, for example. Upon removal of the adhesive support, materials on the surface of the skin, such as skin cells and/or skin excretions, are retained on the adhesive and may be subsequently analyzed, as described below.

In an absorption technique, a porous support may be used to collect solid, liquid, and/or gaseous components of the body portion, such as the outer skin layer (i.e., stratum corneum), for example. The support may be formed of a polymer, a woven fabric, or a nonwoven fabric. Alternatively, the support may comprise an inorganic compound, such as ceramic or rock wool. An example of a porous, inorganic support that could be used for the acquisition and analysis of samples is described in U.S. Provisional Patent Application Ser. No.60/331,003 entitled DISPOSITIF DE MESURE ET/OU D'ANALYSE D'AU MOINS UN PARAMETRE D'UNE PORTION EXTERNE DU CORPS HUMAIN, filed on Nov. 6, 2001, the disclosure of which is incorporated herein by reference. Such a support may be formed of ceramic material, for example.

To acquire a sample through absorption, the support may be placed in contact with a body portion, such as the outer skin layer, for example, for a period of time. Over even a short length of time, liquid secretions from the skin could become retained in the pores of the support and these secretions could be analyzed upon removal of the support.

In one arrangement, the support may be mounted on an adhesive substrate and placed on the skin to provide contact with the skin for a period of time sufficient to acquire a usable sample. The sample may then be extracted from the support for analysis or evaluated while it is retained on the support.

In an abrasion sample collection technique, an abrasive support may be used to collect solid, liquid, and/or gaseous components of the skin and/or hair. The support may comprise a scraping device utilizing one or more blades. Alternatively, the support may comprise a roughened surface formed of an inorganic compound, such as ceramic or rock wool. An example of an abrasive, inorganic support that could be used for the abrasive collection of samples is described in above-mentioned U.S. Provisional Patent Application Ser. No. 60/331,003.

To acquire a sample through abrasion, the support may be placed in contact with a body portion, such as the skin, nail, and/or hair, and then moved while maintaining the contact, for example in a linear or twisting motion. As the support abrades the surface of the skin, nail, and/or hair, components of the skin/nail/hair are collected in the support. Where a bladed device is used, the body portion sample may be retained between a pair of blades. With an inorganic support, the body portion sample may be retained in the pores of the support. After the sample is collected, the sample may be extracted from the support for analysis and/or the sample may be analyzed while still retained on the support.

The samples may be acquired by the subject and/or by at least one provider in the subject's home or at a location remote from the subject's home.

In one example, a subject may acquire samples of her skin and/or hair using an adhesive strip, an absorptive collection device, and/or an abrasive collection device. The subject may then transfer the samples and/or information about the samples to a provider for analysis. For example, the subject may deliver the samples to the provider in person, send them using a package delivery service, such a postal service or a courier, or send information about them electronically. To enable electronic transmission of information about the sample, the subject may use an electronic device to acquire the sample. Such a device may be configured to obtain a sample and generate transmittable data based on the sample's content. The user may then send the data to the provider using a computer network, for example by e-mail or another conventional input/output device.

In another example involving nails and/or hair, a sample of nails and/or hair could be acquired by cutting and/or scraping a sample.

In another example, a provider may acquire samples using any conventional sample collection device. The provider who collected the samples could either analyze the samples or transmit the samples and/or information about the samples to another provider for analysis. Again, the samples may be delivered in person or sent using a postal service or a package delivery service, or information about them may be sent electronically.

When one or more samples are collected, each of the obtaining of the first information (step 20) and the obtaining of the second information (step 22) may further comprise analyzing the sample(s) to ascertain one or more qualitative properties and/or quantitative properties relating to the condition(s). The qualitative properties may relate to the presence or absence of one or more components, and the quantitative properties may relate to the relative quantities of one or more components in the sample. A plurality of properties may be ascertained from the analysis.

The analyzing of the samples may be carried out using any known technique, such as optical, chemical, and biological analysis techniques. For example, the analysis technique may be chosen from gas chromatography/mass spectrometry, gas chromatography/mass spectrometry/mass spectrometry, liquid chromatography/mass spectrometry, liquid chromatography/mass spectrometry/mass spectrometry, ultraviolet observation, fluorescence observation, infrared observation, Raman spectrophotometric observation, and X-ray observation. When multiple analysis techniques are used, the same sample could be analyzed in each technique and/or separate samples could be analyzed.

In another example, a provider may analyze the samples by utilizing one or more analysis techniques to identify the types of components, such as dead skin cells, sebum, and/or sweat, for example, that are present in the sample and to determine their relative quantities.

When the samples are analyzed to determine one or more of their properties, the determining of the difference between the first information and the second information (step 24) may comprise determining at least one difference between one or more properties ascertained from analyzing the sample(s) of the first body portion and one or more properties ascertained from analyzing the sample(s) of the second body portion. For example, the provider may determine the difference in the number of dead skin cells in the samples from each location or determine the difference in relative amounts of a particular enzyme in the samples from each location.

As used herein, the term "obtaining" (for example, in step 20 and step 22 of the exemplary method illustrated with the flow chart of FIG. 1) could include any activity wherein information is received regardless of how the information has been conveyed to the recipient. For example, information could be obtained as a result of a receipt or any form of information transmission including, but not limited to, electronic delivery (e.g., email, facsimile transmission, transfer of information via a computer network, uploading and/or downloading of data, etc.), physical shipment (e.g., via a postal service or parcel delivery service), or personal exchange. Obtaining of information could also relate to direct acquisition of information as a result of usage of a device on an external body portion. For example, when measuring pH of a skin portion, information is obtained by the device used to measure the pH, and information might also be obtained by a person using that device and/or any other person or electronic device receiving any form of information transmission indicating the pH measured by the device.

According to a still further embodiment of the method shown in the flowchart of FIG. 1, each of the obtaining of the first information (step 20) and the obtaining of the second information (step 22) may comprise receiving information chosen from a quantitative measurement of the condition(s), one or more images of the external body portion, and one or more external body portion samples. The information may be received in person, using a postal service or a package delivery service, or using a computer network, for example.

In one example, information acquired from the first and second body portions of a subject may be received by a provider. In this example, the subject may acquire measurements of skin pH, for example, for the first and second body portions and then cause information about the measurements to be delivered to a provider, so that the provider obtains the information. Alternatively, a first provider may acquire an image (e.g., ultrasound image) and/or a sample of first and second body portions of the subject and then cause information relating to the images and/or samples to be delivered to a second provider, so that the second provider obtains the information.

Figure 5:
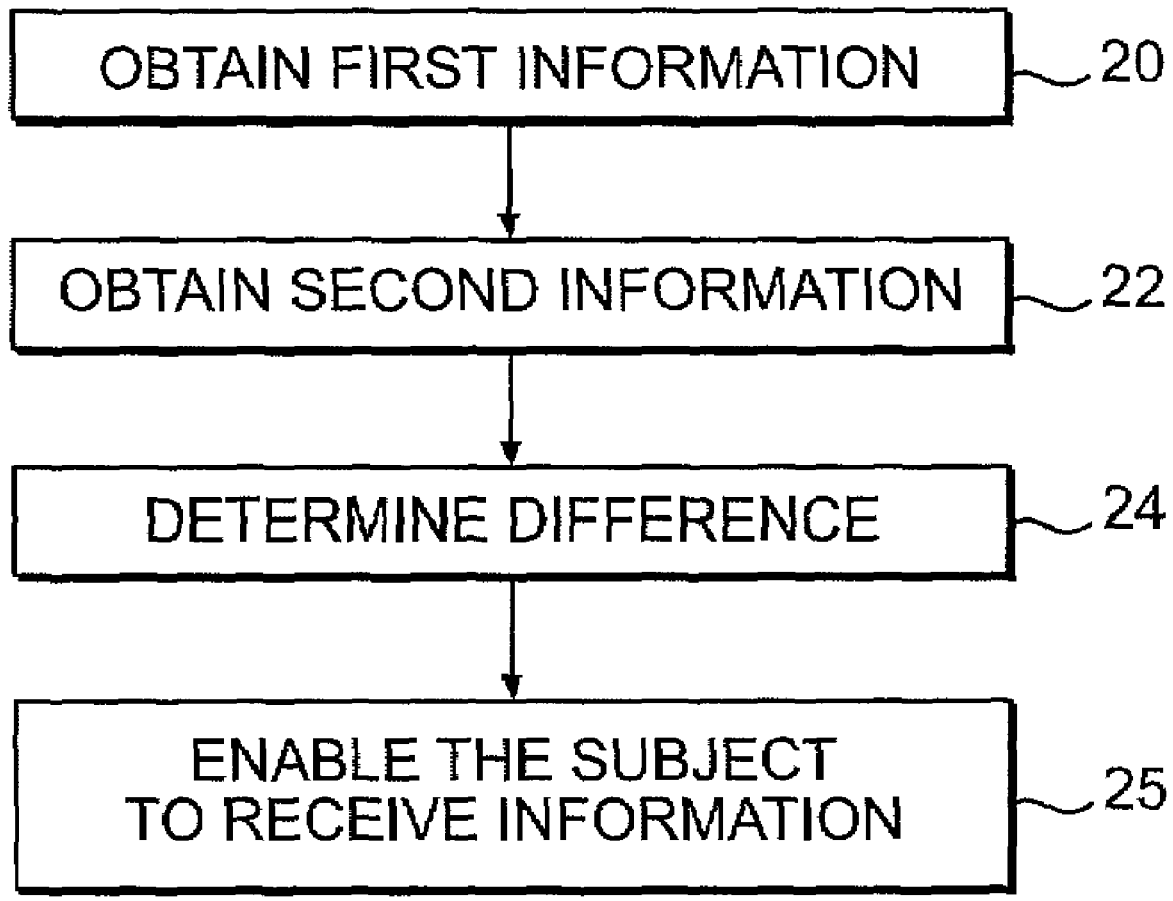
FIG. 5 is an exemplary flowchart illustrating a method in accordance with an exemplary embodiment of the invention.

It should be appreciated that the method depicted in the flowchart of FIG. 1 could have one or more additional steps preceding or following one or more of the steps 20, 22, and 24. For example, FIG. 5 shows a flowchart of an exemplary method wherein after the difference is determined in step 24, the subject is enabled to receive information (step 25). There are many different forms of information that the subject might be enabled to receive. For example, the information might be an indication of the difference determined in step 24, and/or a notification about the impact of environmental factors affecting the first external body portion, and/or information about one or more products that could be used for the first external body portion.

In another example, the information could be any form of information that permits the subject to determine her potential for improving her appearance by using the subject herself as a baseline, as opposed to someone else.

In a further example, the information may relate to a product, such as a cosmetic product, care product, pharmaceutical, and/or other product. According to this example, a product may be applied to the first and second external body portions of the subject. Where the first and second external body portions have different levels of exposure to one or more environmental factors and/or other factors, the determining of the difference between the first information and the second information may provide information about the performance (e.g., efficacy) of the product. This information may include the performance of the product as a function of different levels of environmental exposure, for example.

Figure 7:
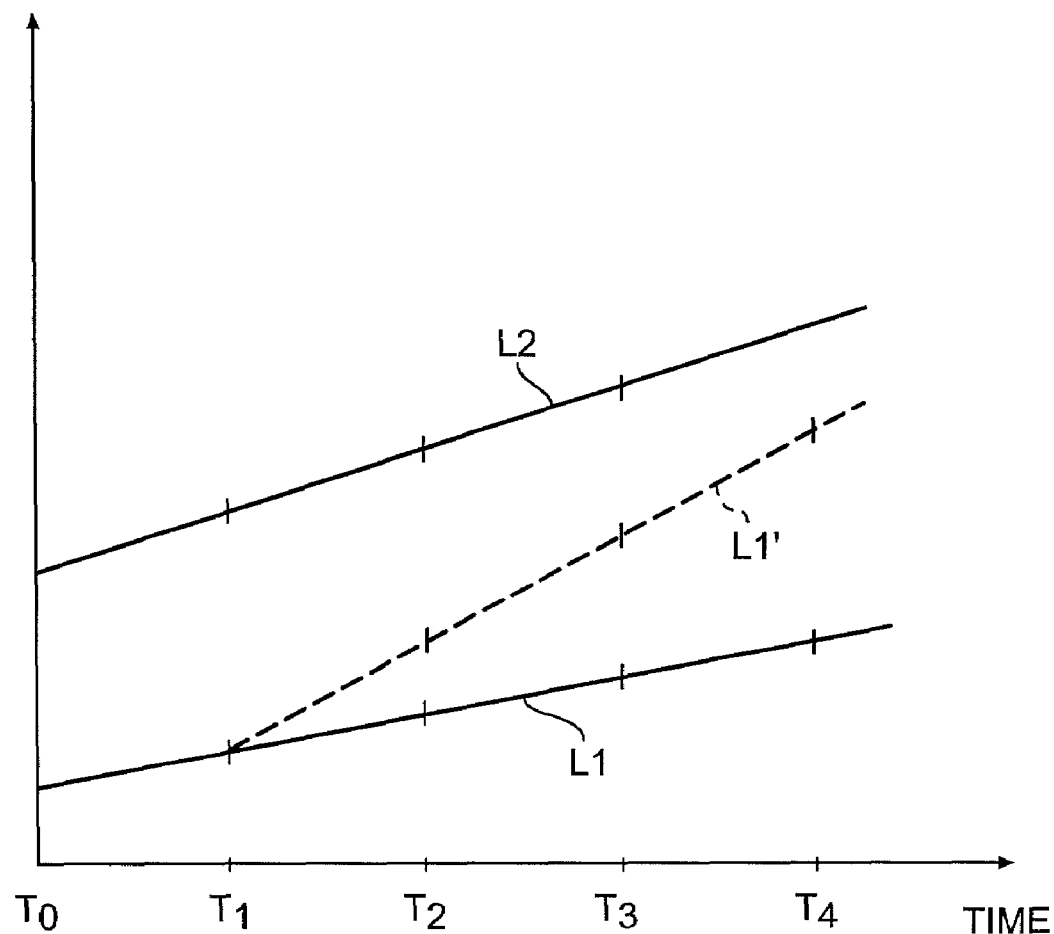
FIG. 7 is an exemplary graphic illustration in accordance with an exemplary embodiment of the invention.

FIG. 7, which is explained below, shows an example of a graphical illustration that might be provided to the subject as a result of step 25 of FIG. 5.

Figure 6:
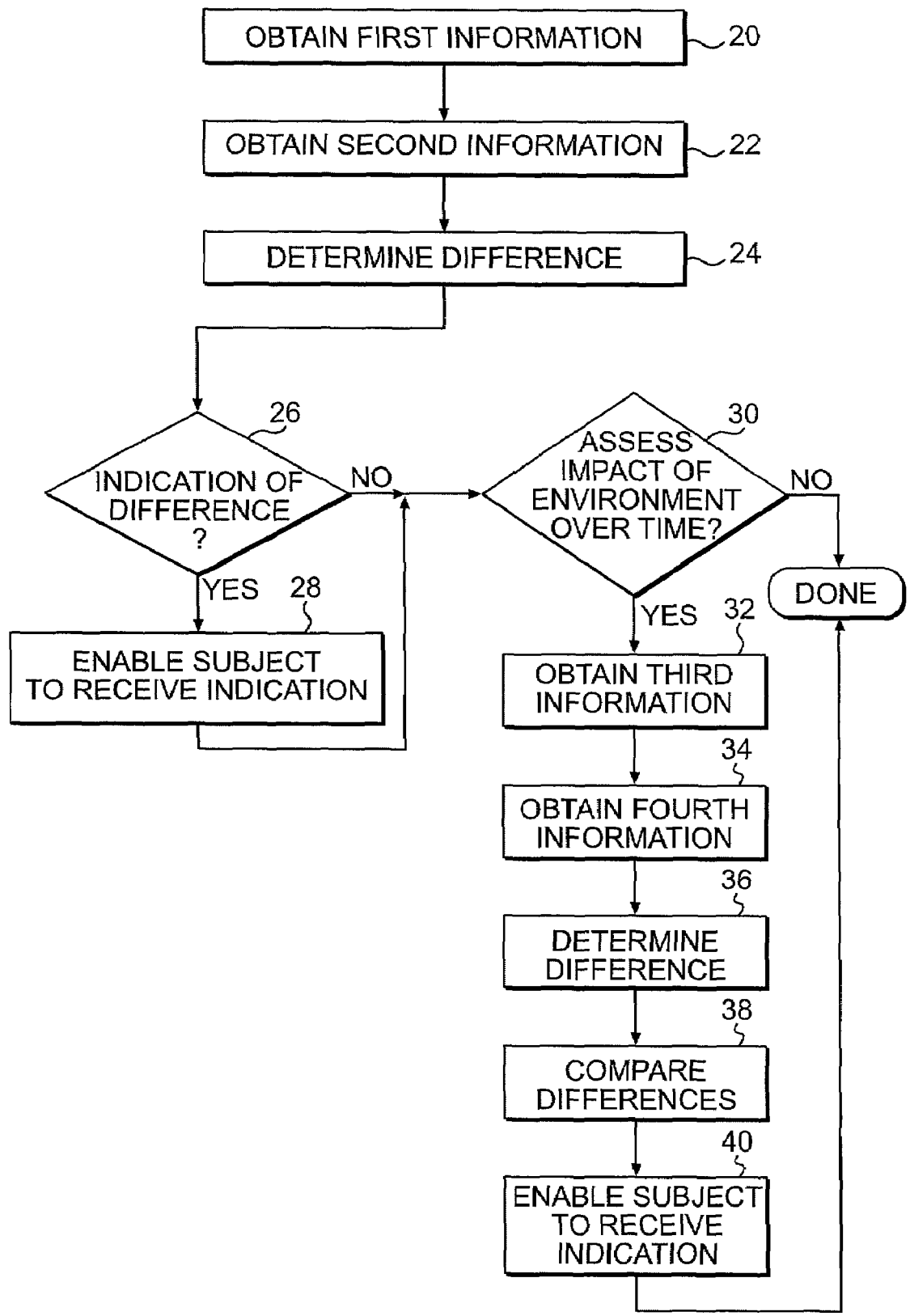
FIG. 6 is an exemplary flowchart illustrating a method in accordance with an exemplary embodiment of the invention.

The flowchart in FIG. 6 shows a further exemplary embodiment of the invention. As shown, after the steps 20, 22, and 24, described above, have been performed, the subject may be given the option to receive an indication of the difference between the first information and the second information (step 26). Since this difference may correlate to the impact of one or more environmental factors on the first body portion, a viewing of the difference might provide an indication of environmental impact on the first body portion.

If that option is chosen, the subject may be enabled to receive an indication of the difference (step 28). In one example, the subject may visit the provider in person and the provider could explain the difference. In another example, the subject could be provided with an opportunity to view the difference in the form of some visual indication. One example of a visual indication is the graphic illustration of FIG. 7, described in more detail below.

Alternatively, the indication may be illustrated using images of the subject's first body portion. For example, one image may show the subject's first body portion with the measured conditions, while another image may show a simulated image of the first body portion having the conditions of the second body portion. These two images may represent, respectively, a baseline image showing existing conditions and an ideal image showing the potential benefits of the treatment. According to this example, a picture of the subject's face in substantially its current condition may be provided along with a virtual image showing the face having one or more conditions of the second body portion. These contrasted images may provide the subject with a realistic expectation of the results of a skin treatment, for example.

A provider may enable a subject to receive an indication of the difference between the first information and the second information by sending it to the subject. The indication may be sent using a package delivery service, such as a courier or the postal service. The indication may be a hard copy of a graphic illustration or stored information relating to the indication on a computer readable medium, such as a disk or tape, containing a digital copy of the graphic illustration.

The provider may also utilize a computer network to send the indication to the subject. Here, the provider may send the indication, such as a digital copy of the graphic illustration, using e-mail. Alternatively, the provider may make the indication available on a website that the subject may access. The indication may be made available on the website in any conventional form, including graphical illustrations or numerical listings.

After completing step 28, or if the subject chooses not to receive an indication of the difference between the first information and the second information (step 26), the subject may be given the option to assess the impact of the environment on the first body portion over time (step 30).

If the subject chooses to assess the impact of the environment on the first body portion over time (step 30), further steps of the method may be performed. The first information obtained in step 20 may be representative of the one or more conditions of the first external body portion of the subject at approximately a first time. Further, the second information obtained in step 22 may be representative of one or more conditions of the second external body portion of the subject at approximately the first time. As shown in FIG. 6, the further steps may comprise obtaining third information, which is representative of the one or more conditions of the first external body portion of the subject at approximately a second time (step 32), obtaining fourth information, which is representative of the one or more conditions of the second external body portion of the subject at approximately the second time (step 34), and determining a difference between the third information and the fourth information (step 36). Here, the third information and fourth information could be initially acquired and obtained in the same way in which the first and second information were acquired and obtained, by using the same types of device(s).

In this example, the third information and fourth information relate to one or more conditions existing at approximately a second time occurring a period of time after the approximate first time relating to the first information and the second information. For example, the period of time could be in terms of hours, days, months, and/or years. Although the first/second information and third/fourth information may relate to one or more conditions existing at differing periods of time, this information may be obtained simultaneously, for example, by receiving a single data transmission containing each of the first, second, third, and fourth information, and/or at different times, for example, by receiving a first data transmission containing the first/second information and a second data transmission containing the third/fourth information.

As shown in FIG. 6, the method could further include comparing the difference between the first information and the second information with the difference between the third information and the fourth information so as to enable an analysis taking into account impact of the environmental factor(s) over at least the period of time (step 38). The subject may then be enabled to receive an indication of the impact of one or more environmental factors over time (step 40).

This indication may be in the form of a graphic illustration, such as that shown in FIG. 7, where the condition (in some quantifiable form) is charted over time with a better condition having a greater value. In FIG. 7, the first portion line L1 represents the condition of a first body portion over time and the second portion line L2 represents the condition of a second body portion over time. For this example, the lines L1 and L2 diverge, showing that the impact of one or more environmental factors may become more pronounced over time. Time $T_0$ represents the approximate time at which the first and second information were obtained and time $T_1$ represents the approximate time at which the third and fourth information were obtained.

As shown in FIG. 7, further information about the condition of the first and second body portions could also be obtained at later times $T_2$, $T_3$, $T_4$, etc. and added to the chart. Alternatively, data processing, such as extrapolation, could be used to estimate the condition at these times. The length of time of each time period $T_0$-$T_1$, $T_1$-$T_2$, etc. could be any length, but at least some examples of the method may have time periods of at least a few days, weeks, months, or years.

The method described with reference to FIG. 6 may be carried out with external body portions that have received a treatment, such as an application of a product. In addition (or in the alternative), the method may be practiced with untreated external body portions.

In another example of the method, the subject may assess the impact of the environment on the first body portion over time by obtaining third information, which is representative of one or more conditions of the first external body portion of the subject at approximately a second time and determining a difference between the third information and the second information. This difference may be compared with the difference between the first and second information so as to enable an analysis taking into account impact of the environmental factor(s) over at least the period of time. Thus, in this example, optionally no additional information representative of the condition(s) of the second external body portion is obtained.

Other examples of the method may have time periods of relatively short duration, such as minutes or seconds. Obtaining information at short intervals may provide kinetic (e.g., dynamic) characterization of the conditions of the external body portions. In one example, the pH of skin located on the face and skin located on the buttocks may be measured every 10 seconds for an hour or longer. This kinetic measurement of the pH may enable construction of a curve representative of the condition for each external body portion over time. The curves for each external body portion may be compared to determine the difference between one or more conditions of the portions.

The graphic illustration of FIG. 7 also includes a prediction line L1'. The prediction line L1' could be a representation of a prediction of the condition of the first portion if a product is used to treat the first portion after time $T_1$. Rather than sloping away from the second portion line L2, like the first portion line L1, the prediction line L1' slopes toward second portion line L2, thereby illustrating how use of a product might reduce the impact of the environmental factor(s) on the first portion. For example, when the condition is wrinkles, the prediction line L1' might provide a representation of the improvement of wrinkles in the first portion if a wrinkle reducing product is applied to the first portion. In addition to enabling the subject to receive the graphical illustration of FIG. 7, the subject might also be enabled to receive information about the product forming the basis for the prediction line L1', such as an identification of the product and also, optionally, information enabling the subject to purchase the product.

After completing step 40 of FIG. 6, or if the subject chooses not to assess the impact of the environment on the first body portion over time (step 30), the method of this embodiment may be complete. Alternatively, when further information is obtained at a later time, the method could continue.

Figure 8:
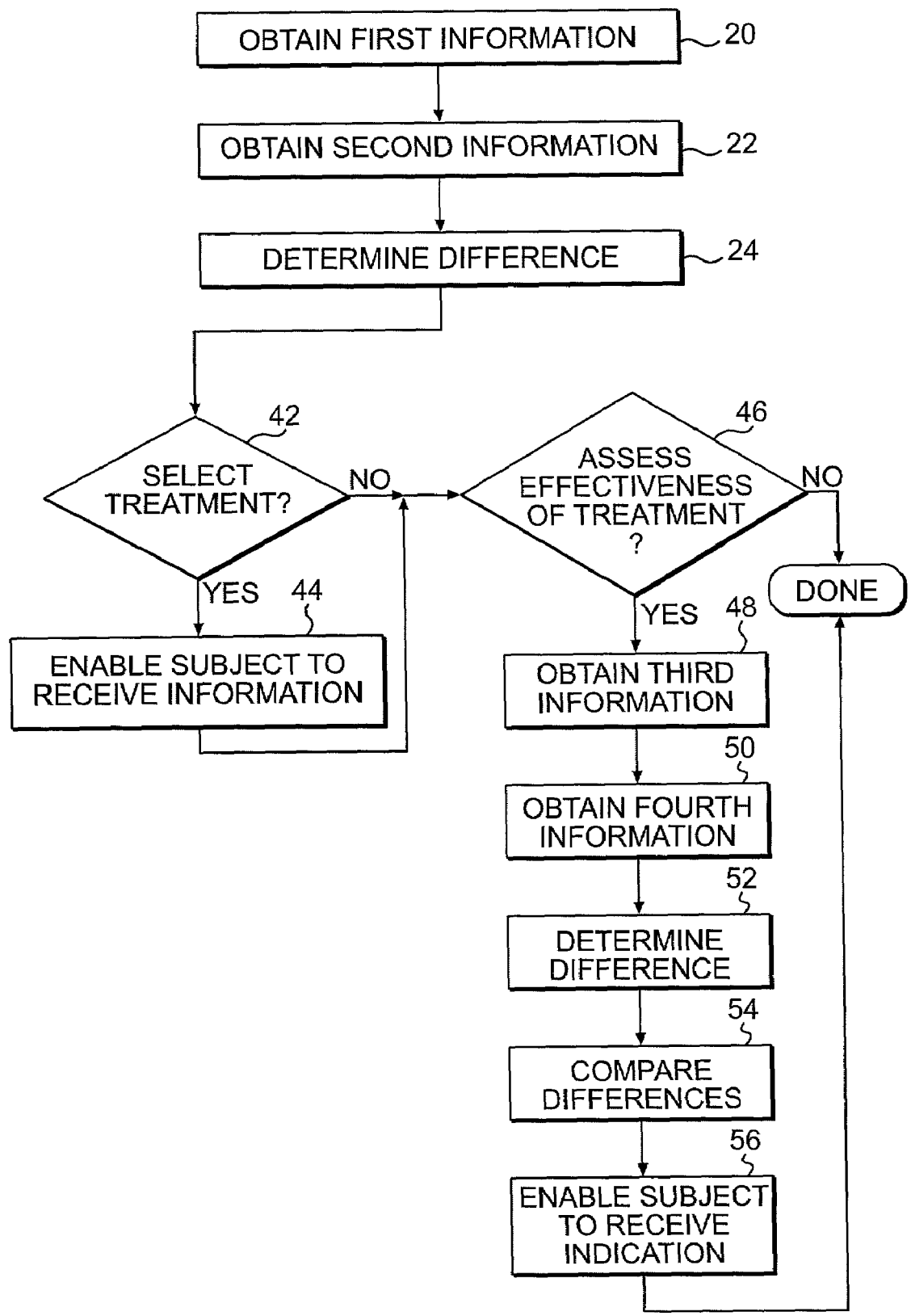
FIG. 8 is an exemplary flowchart illustrating a method in accordance with an exemplary embodiment of the invention.

The flowchart in FIG. 8 shows a further exemplary embodiment of the invention. As shown, after performing the steps 20, 22, and 24, the subject may be given the option to select a treatment for the first external body portion based on the difference between the first information and the second information (step 42).

If that option is chosen, the subject may be enabled to receive information regarding a recommended treatment of the first external body portion (step 44). The recommended treatment may comprise applying a cosmetic product and/or a care product to the first external body portion.

In one example, the subject may visit the provider in person and the provider may recommend the treatment during a discussion. In another example, the provider may enable a subject to receive information regarding the recommended treatment by sending it to the subject. The information may be sent using a package delivery service, such as a courier or a postal service. The information may be a hard copy or digital information relating to the treatment.

The provider may also utilize a computer network to send the information to the subject. For example, the provider may send the information, such as a digital copy of the information, using e-mail. Alternatively, the provider may make the information available on a website that the subject may access. The information may be made available on the website in any conventional form, including graphical illustrations having hypertext or text descriptions.

After completing step 44, or if the subject chooses not to receive information regarding the recommended treatment of the first external body portion (step 42), the subject is given the option to assess at least initial effectiveness of the treatment (step 46).

If the subject chooses to assess at least initial effectiveness of the treatment (step 46), further steps of the method may be performed. The first information obtained in step 20 may be representative of the one or more conditions of the first external body portion of the subject at approximately a first time. Further, the second information obtained in step 22 may be representative of the one or more conditions of the second external body portion of the subject at approximately the first time. As shown in FIG. 8, the method may further comprise obtaining third information, which is representative of the condition(s) of the first external body portion of the subject at approximately a second time (step 48), obtaining fourth information, which is representative of the condition(s) of the second external body portion of the subject at approximately the second time (step 50), and determining a difference between the third information and the fourth information (step 52). The second time may occur at least a period of time after a treatment of the first external body portion is initiated. Thus, the third information and the fourth information of the method of FIG. 8 may relate to one or more conditions existing at least a period of time after a treatment of the first external body portion is initiated.

Figure 9:
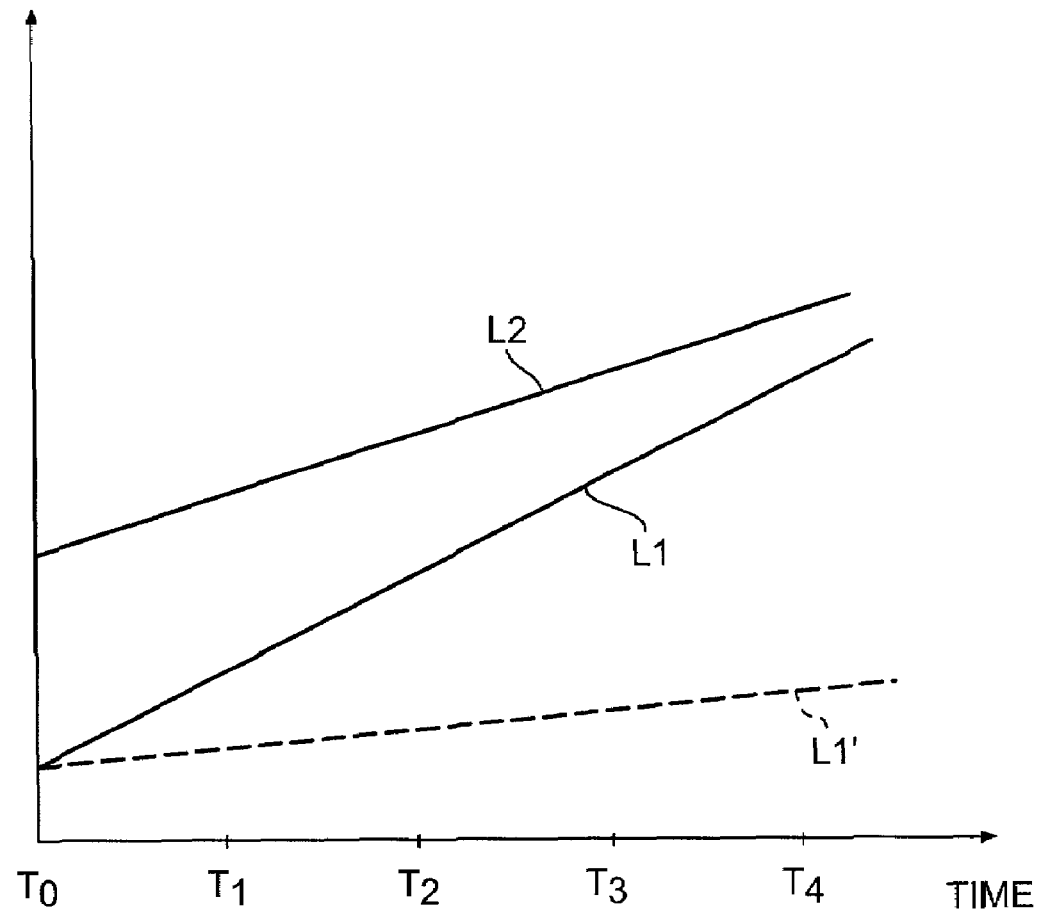
FIG. 9 is an exemplary graphic illustration in accordance with an exemplary embodiment of the invention.

As shown in FIG. 8, the method may further comprise comparing the difference between the first information and the second information with the difference between the third information and the fourth information so as to enable a determination of at least initial effectiveness of the treatment (step 54). The subject may then be enabled to receive an indication of at least initial effectiveness of the treatment (step 56). This indication may be in the form of a graphic illustration, such as that shown in FIG. 9, wherein the first portion line L1 could represent the condition of the first portion as a result of the treatment, the second portion line L2 could represent the condition of the second portion, and the prediction line L1' could represent a prediction of the condition of the first portion if the treatment is discontinued. Alternatively, the graphic illustration could be like that of FIG. 7, wherein the prediction line L1' of FIG. 7 represents a prediction of the condition of the first portion if the treatment of the first portion is altered to include a second product differing from the product of the initial treatment and/or to include a product dosage and/or product application method differing from that initially used.

After completing step 56, or if the subject chooses not to assess at least initial effectiveness of the treatment (step 46), the method of FIG. 8 may be complete. Optionally, certain additional method steps, such as further information obtaining, might be performed in the process before completing it.

Optionally, any of the methods described herein may comprise recommending a product based on the difference between the first information and the second information, and may also comprise determining at least the initial effectiveness of the product after it is applied to the first portion.

Any of the disclosed methods may also further comprise enabling the subject to receive information regarding at least one product capable of reducing the impact of the at least one environmental factor. The product information may be communicated to the subject using at least one of a package delivery service and a computer network. Further, the product may be offered for sale to the subject and/or the subject may be provided with information, in any manner described above, for example, to enable the subject to purchase the product.

Information representative of multiple conditions of the external body portions may be collected using one or more of the above-described methods. This information may then be correlated to provide a more detailed assessment of the first external body portion and how it compares with the second external body portion. The information may be further correlated with the sensory observations of the subject to aid in the assessment of the effectiveness of the treatment.

Figure 10:
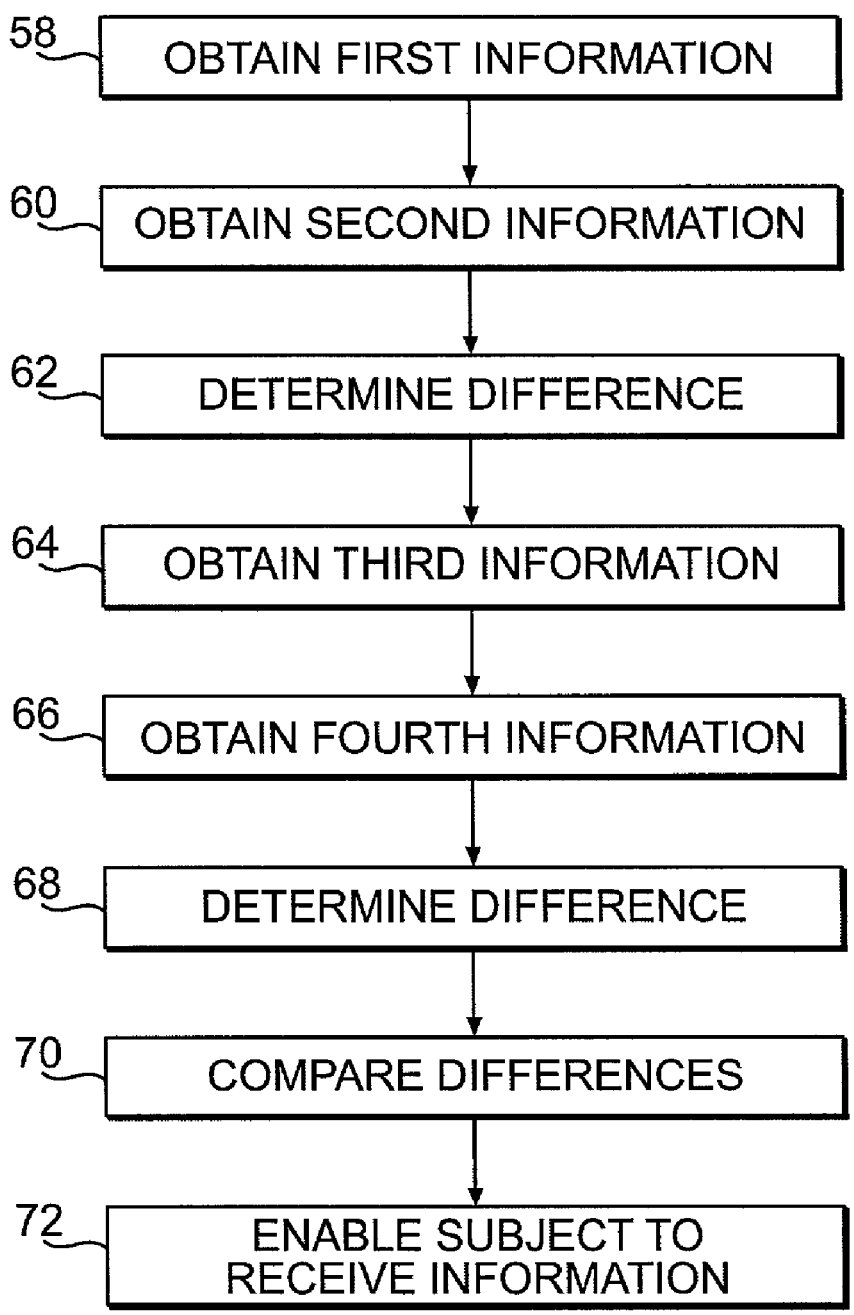
FIG. 10 is an exemplary flowchart illustrating a method in accordance with an exemplary embodiment of the invention.

The flowchart in FIG. 10 shows a further exemplary method. The method may comprise obtaining first information, which is representative of one or more conditions of a first external body portion of a subject at approximately a first time (step 58), obtaining second information, which is representative of one or more conditions of a second external body portion of the subject at approximately the first time (step 60), and determining a difference between the first information and the second information (step 62), which could be performed as discussed above in association with FIG. 1.

The method of FIG. 10 may further comprise obtaining third information, which is representative of the one or more conditions of the first external body portion at approximately a second time (step 64), obtaining fourth information, which is representative of the one or more conditions of the second external body portion at approximately the second time (step 66), determining a difference between the third information and the fourth information (step 68), and comparing the difference between the first information and the second information with the difference between the third information and the fourth information (step 70). The second time may occur at least a period of time after a treatment of the first external body portion is initiated. Thus, for the method shown in FIG. 8, the third and fourth information may relate to one or more conditions existing at least a period of time after a treatment of the first external body portion is initiated.

The treatment could be initiated either approximately at the first time, before the first time, or after it. In one possible example, the obtaining of the third information (step 64) and the obtaining of the fourth information (step 66) may occur at least a period of time after the treatment of the first external body portion is initiated. The subject may then be enabled to receive an indication of at least initial effectiveness of the treatment (step 72), as described above in association with FIG. 8.

The one or more initial conditions of the first external body portion may be substantially absent from the second external body portion. The one or more conditions may include eczema, psoriasis, acne, and/or atopic dermatitis. The treatment may comprise administering at least one pharmaceutical compound to the first external body portion.

Any of the methods described herein may further comprise maintaining a database containing external body portion information for a plurality of subjects and conducting an analysis based on a comparison between information in the database and at least one of the first information, the second information, and the determined difference. At least one of the first information, the second information, and the determined difference may be stored in the database.

Optionally, any of the methods might also include maintaining a subject record and causing storage in the subject record of at least one of the first information, the second information, and the determined difference. Information acquired subsequent to the first information and the second information could be stored in this subject record. The subject may also be enabled to access at least a portion of information stored in the subject record via at least one of a package delivery service and a computer network, as described above.

In some examples, the method may provide the ability to compare two differing external body portions at differing times (e.g., $T_0$, $T_1$, $T_2$, $T_3$, etc.), either with or without a treatment (e.g., a cosmetic treatment, such as a cosmetic product application) being applied to the first external body portion.

Some examples of the method may allow for potential correlation of multiple differing parameters (e.g., bioanalytical, bioinstrumental, clinical, and/or sensorial parameters) at differing times (e.g., $T_0$, $T_1$, $T_2$, $T_3$, etc.) either with or without a treatment being applied to the first external body portion. For example, multiple tests (e.g., a pH test and a sensorial touch test) could be made on each portion and the data could be used to determine a correlation.

Some examples of the method might enable an analysis of the kinetic evolution of one or more parameters (e.g., bioinstrumental and/or bioanalytical) of the external body portions either with or without a treatment being applied to the first portion.

Figure 11:
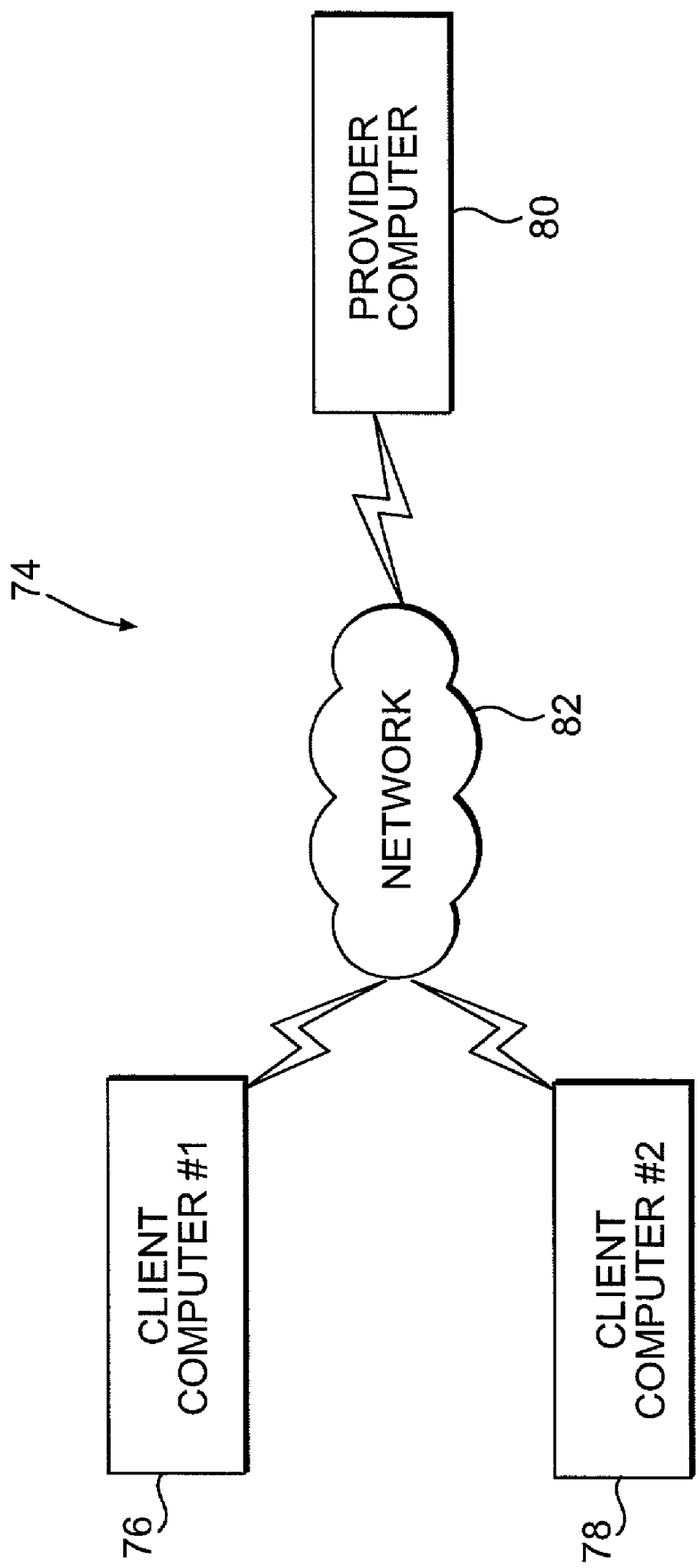
FIG. 11 is an exemplary block diagram of a computer system.

An exemplary block diagram of a computer system 74 suitable for performing at least portions of the methods of the present invention is shown in FIG. 11. As shown, there are a plurality of client computers 76, 78 that may be used to initially acquire information relating to the first and second external body portions of the subject, and a provider computer 80 that may obtain the information and determine the difference. This computer system 74 may comprise a different number of computers than are shown. The client computers 76, 78 may interface with the provider computer 80 via a network 82.

Each client computer 76, 78 may be capable of communicating with other computers. The client computers 76, 78 may be used to perform various tasks. Each client computer 76, 78 may include a browser, such as Internet Explorer or Netscape Navigator to assist the user in performing these tasks. In the example illustrated in FIG. 11, one client computer ("Client Computer #1") is configured for use by the subject and another client computer ("Client Computer #2") is configured for use by a first provider, who might be an entity that initially acquires information about the first and second external body portions. Different numbers of each type of computer may be used to perform one or more parts of the method or the entire method.

The provider computer 80 may be a Sun Enterprise 4500 server or any other processor capable of communicating with other computers.

The network 82 may include a Local Area Network (LAN) or a Wide Area Network (WAN). In addition, the network 82 may also include a combination of public (e.g., Internet) and private networks.

Other system and network configurations will be apparent to those skilled in the art and are also within the scope of the present invention. For example, the system 74 as shown in FIG. 11 may include more than one provider computer 80 to provide load balancing and fail-over capabilities. In a further example, the system may lack one of the client computers 76, 78. Moreover, it will be apparent to one skilled in the art that the components shown in FIG. 11 may use various protocols, such as Hypertext Transport Protocol (HTTP) and Transmission Control Protocol/Internet Protocol (TCP/IP) to communicate with each other.

Figure 12:
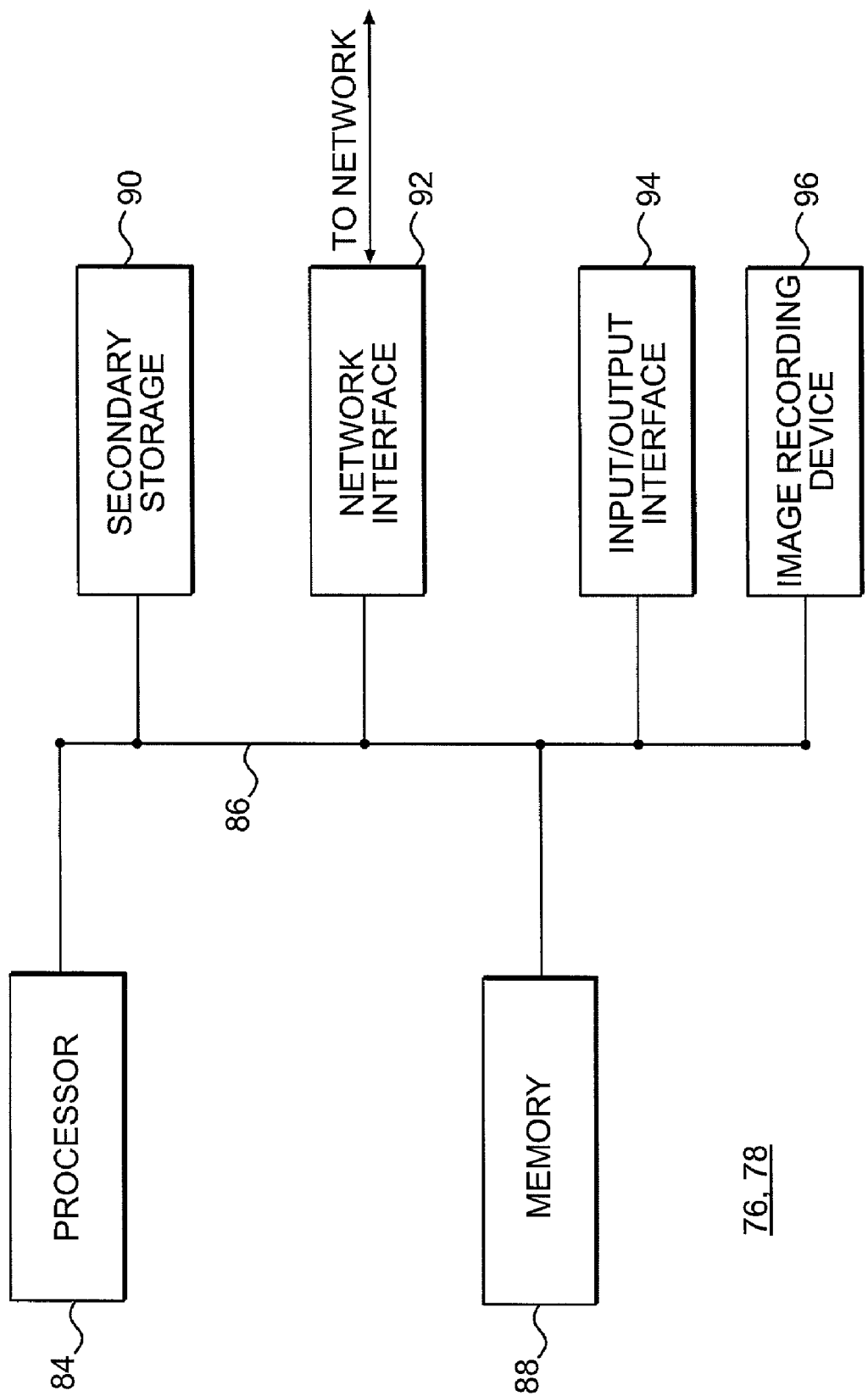
FIG. 12 is an exemplary block diagram of a client computer.

FIG. 12 is an exemplary block diagram of the client computer 76, 78. The client computer 76, 78 may comprise a processor 84, which connects via a bus 86 to a memory 88, a secondary storage 90, a network interface 92, an input/output interface 94, and an image recording device 96. The image recording device 96 may comprise an image scanner, a digital video camera, a digital camera, and/or other conventional device.

The client computer 76, 78 may be configured to operate with any known operating system, including, for example, the Solaris operating system available from Sun Microsystems, Inc., the Linux operating system, or a Windows operating system (e.g., Windows NT).

The client computer may be associated with a secondary storage 90 permitting use of a computer readable medium, such as a disk or a tape. Software and/or data may be loaded into memory from the computer readable medium.

The network interface 92 may transmit messages from the client computer 76, 78 to other computers, such as other client computers and/or the provider computer 80, and may receive messages addressed to the client computer 76, 78 from other computers, for example, via the network 82. The input/output interface 94 may include, for example, a keyboard or a key pad and a display unit.

Figure 13:
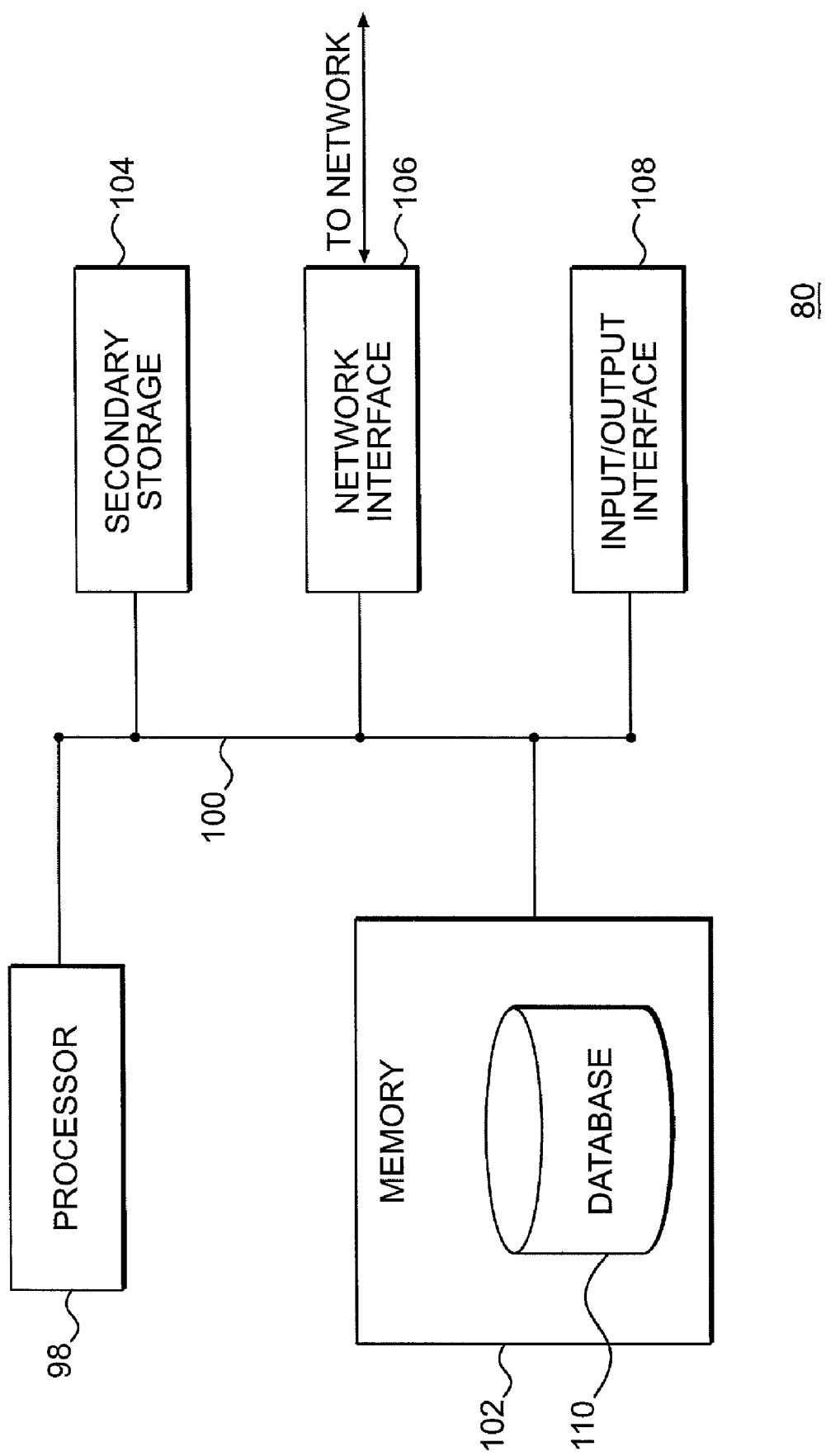
FIG. 13 is an exemplary block diagram of a provider computer.

FIG. 13 is an exemplary block diagram of the provider computer 80. The provider computer 80 may comprise a processor 98, which connects via a bus 100 to a memory 102, a secondary storage 104 permitting use of a computer readable medium, a network interface 106, and an input/output interface 108.

The provider computer 80 may operate with any known operating system. The operating system may include, for example, the Solaris operating system, the Linux operating system, or a Windows operating system (e.g., Windows NT).

The memory 102 may include a database 110. The database 110 may contain external body portion information for a plurality of subjects, as described above. A variety of analyses may be performed by comparing information in the database 110 with the first information, the second information, and the determined difference. The database 110 may also contain one or more subject records, as described above.

The memory 102 may also include a relational database management system, such as Oracle 8i version 8.1.6 available from Oracle Corporation or Ingres, available from Computer Associates International, Inc.

The network interface 106 may transmit messages from the provider computer 80 to other computers, such as client computers, and receive messages addressed to the provider computer 80 from other computers, for example, via networks. The input/output interface 106 may include, for example, a keyboard or a key pad and a display unit.

Other embodiments of the invention will be apparent to those skilled in the art from consideration of the specification and practice of the invention disclosed herein. It is intended that the specification and examples be considered as exemplary only.

What is claimed is:

1. A method of enabling an analysis taking into account exposure of at least one external body portion to the environment, the method comprising:
    obtaining first information representative of at least one condition of a first external body portion of a subject;
    obtaining second information representative of at least one condition of a second external body portion of the subject, wherein the second external body portion is normally less exposed to at least one environmental factor than the first external body portion;
    determining a difference between the first information and the second information so as to enable an analysis taking into account impact of the at least one environmental factor;
    obtaining third information, wherein the third information is representative of the at least one condition of the first external body portion at least a period of time after a treatment of the first external body portion is initiated; and
    determining a difference between the third information and the second information.

2. The method of claim 1, wherein the at least one condition comprises at least one of texture, elasticity, dryness, cellulitis, sweating, aging, wrinkles, exfoliation, desquamation, homogeneity of color, micro-circulation, shininess, softness, smoothness, hydration, sebum production, cleanliness, irritation, redness, vasomotion, vasodilation, vasoconstriction, pigmentation, and freckles.

3. The method of claim 1, further comprising enabling the subject to receive an indication of the difference between the first information and the second information.

4. The method of claim 3, further comprising sending the indication to the subject via at least one of a package delivery service and a computer network.

5. The method of claim 3, wherein the indication comprises a graphic illustration.

6. The method of claim 1, further comprising selecting the treatment for the first external body portion based on the difference between the first information and the second information.

7. The method of claim 6, wherein the treatment comprises applying at least one of a cosmetic product and a care product to the first external body portion.

8. The method of claim 6, further comprising enabling the subject to receive information regarding the treatment for the first external body portion.

9. The method of claim 1, further comprising comparing the difference between the first information and the second information with the difference between the third information and the second information so as to enable a determination of at least initial effectiveness of the treatment.

10. The method of claim 9, further comprising enabling the subject to receive an indication of the at least initial effectiveness of the treatment.

11. The method of claim 1, further comprising recommending at least one product based on the difference between the first information and the second information.

12. The method of claim 11, further comprising enabling the subject to receive information regarding the at least one product.

13. The method of claim 12, wherein the product information is communicated to the subject using at least one of a package delivery service and a computer network.

14. The method of claim 12, further comprising at least one of offering the at least one product for sale to the subject and providing the subject with information enabling the subject to purchase the at least one product.

15. The method of claim 1, wherein the at least one environmental factor is chosen from ultraviolet radiation, extreme temperature, wind, pollution, and shaving.

16. The method of claim 15, wherein the at least one environmental factor comprises a plurality of environmental factors.

17. The method of claim 1, wherein the first external body portion comprises skin located on the face of the subject, and the second external body portion comprises one of skin located on the upper buttocks of the subject and skin located on an inner surface of an upper part of at least one of the subject's arms.

18. The method of claim 1, wherein the first external body portion comprises at least one of hair and skin located on the scalp of the subject and the second external body portion comprises at least one of hair and skin located in the pubic area of the subject.

19. The method of claim 1, wherein the first external body portion comprises a fingernail and the second external body portion comprises a toenail.

20. The method of claim 1, wherein the first external body portion comprises a first portion of a hair on the subject's scalp and the second external body portion comprises a second portion of the hair on the subject's scalp.

21. The method of claim 1, wherein the first external body portion comprises a first portion of a fingernail and the second external body portion comprises a second portion of the fingernail.

22. The method of claim 1, wherein the first external body portion comprises a first portion of a toenail and the second external body portion comprises a second portion of the toenail.

23. The method of claim 1, wherein each of the obtaining of the first information and the obtaining of the second information comprises acquiring a quantitative measurement of the at least one condition.

24. The method of claim 23, wherein the quantitative measurement is chosen from corneometry, dermal torque measurement, pH measurement, colorimetry, sebumetry, lipometry, confocal measurement, epidermal turnover measurement, skin layer thickness measurement, blood microcirculation measurement, desquamation rate measurement, water loss measurement, skin hydration measurement, scoring with a densiscore-type tool, and measurement of sudatory function.

25. The method of claim 23, wherein the determining of the difference between the first information and the second information comprises determining at least one difference between the quantitative measurement of the at least one condition of the first external body portion and the quantitative measurement of the at least one condition of the second external body portion.

26. The method of claim 1, wherein each of the obtaining of the first information and the obtaining of the second information comprises acquiring at least one image of a respective external body portion of the subject.

27. The method of claim 26, wherein the at least one image is chosen from photographs, scanned images, ultrasonic images, magnified images, wrinkle projections, and imprints.

28. The method of claim 26, wherein each of the obtaining of the first information and the obtaining of the second information further comprises analyzing the at least one image to ascertain at least one of a qualitative property and a quantitative property relating to the at least one condition.

29. The method of claim 28, wherein the analyzing of the at least one image comprises at least one of counting sebaceous glands, counting sweat glands, and visualizing imprints in the at least one image.

30. The method of claim 28, wherein the determining of the difference between the first information and the second information comprises determining at least one difference between at least one property ascertained from analyzing at least one image of the first external body portion and at least one property ascertained from analyzing at least one image of the second external body portion.

31. The method of claim 1, wherein each of the obtaining of the first information and the obtaining of the second information comprises acquiring at least one external body portion sample.

32. The method of claim 31, wherein the at least one sample is chosen from skin cells, hair cells, fingernail cells, toenail cells, secretions, bioanalytical content, bacteriological content, and enzymatic content.

33. The method of claim 31, wherein the acquiring of the at least one sample is carried out using a technique chosen from adhesive collection, absorption, and abrasion.

34. The method of claim 31, wherein each of the obtaining of the first information and the obtaining of the second information further comprises analyzing the at least one sample to ascertain at least one of a qualitative property and a quantitative property relating to the at least one condition.

35. The method of claim 34, wherein the qualitative property relates to one of presence and absence of at least one component, and the quantitative property relates to relative quantity of at least one component in the sample.

36. The method of claim 34, wherein the analyzing of the at least one sample is carried out using at least one of an optical, chemical, and biological analysis technique.

37. The method of claim 36, wherein the analysis technique is chosen from gas chromatography/mass spectrometry, gas chromatography/mass spectrometry/mass spectrometry, liquid chromatography/mass spectrometry, liquid chromatography/mass spectrometry/mass spectrometry, ultraviolet observation, fluorescence observation, infrared observation, Raman spectrophotometric observation, and X-ray observation.

38. The method of claim 34, wherein the determining of the difference between the first information and the second information comprises determining at least one difference between at least one property ascertained from analyzing at least one sample of the first body portion and at least one property ascertained from analyzing at least one sample of the second body portion.

39. The method of claim 1, wherein each of the obtaining of the first information and the obtaining of the second information comprises receiving information chosen from a quantitative measurement of the at least one condition, at least one image of a respective external body portion of the subject, and at least one external body portion sample.

40. The method of claim 39, wherein each of the obtaining of the first information and the obtaining of the second information further comprises at least one of analyzing the at least one image to ascertain at least one of a qualitative property and a quantitative property relating to the at least one condition and analyzing the at least one sample to ascertain at least one of a qualitative property and a quantitative property relating to the at least one condition.

41. The method of claim 39, wherein the information is received via at least one of a package delivery service and a computer network.

42. The method of claim 1, further comprising:
maintaining a database containing external body portion information for a plurality of subjects; and
conducting an analysis based on a comparison between information in the database and at least one of the first information, the second information, and the determined difference.

43. The method of claim 42, further comprising storing at least one of the first information, the second information, and the determined difference in the database.

44. The method of claim 1, further comprising:
maintaining a subject record; and
causing storage in the subject record of at least one of the first information, the second information, and the determined difference.

45. The method of claim 44, further comprising causing storage in the subject record of subject information acquired subsequent to the first information and the second information.

46. The method of claim 44, further comprising enabling the subject to access at least a portion of information stored in the subject record.

47. The method of claim 46, further comprising enabling the subject to access the information via at least one of a package delivery service and a computer network.

48. The method of claim 46, further comprising enabling the subject to graphically display the information.

49. The method of claim 1, wherein the treatment of the first external body portion comprises applying a product to the first external body portion of the subject.

50. The method of claim 49, further comprising applying the product to the second external body portion of the subject.

51. The method of claim 1, wherein the first external body portion has had a product applied thereto, and wherein the determining of the difference between the first information and the second information provides information about the product.

52. The method of claim 1, wherein the first external body portion and the second external body portion have had a product applied thereto, and wherein the determining of the difference between the first information and the second information provides information about the product.

53. A method of enabling an analysis taking into account exposure of at least one external body portion to the environment, the method comprising:
obtaining first information representative of at least one condition of a first external body portion of a subject, wherein the first information is representative of the at least one condition of the first external body portion of the subject at approximately a first time;
obtaining second information representative of at least one condition of a second external body portion of the subject, wherein the second information is representative of the at least one condition of the second external body portion of the subject at approximately the first time, and wherein the second external body portion is normally less exposed to at least one environmental factor than the first external body portion;

determining a difference between the first information and the second information so as to enable an analysis taking into account impact of the at least one environmental factor;

obtaining third information, wherein the third information is representative of the at least one condition of the first external body portion of the subject at approximately a second time, wherein the second time occurs at least a period of time after the first time; and determining a difference between the third information and the second information.

54. The method of claim 53, further comprising comparing the difference between the first information and the second information with the difference between the third information and the second information so as to enable an analysis taking into account impact of the at least one environmental factor over at least the period of time.

55. The method of claim 54, further comprising enabling the subject to receive an indication of the impact of the at least one environmental factor over at least the period of time.

56. A method of enabling an analysis taking into account exposure of at least one external body portion to the environment, the method comprising:

obtaining first information representative of at least one condition of a first external body portion of a subject, wherein the first information is representative of the at least one condition of the first external body portion of the subject at approximately a first time;

obtaining second information representative of at least one condition of a second external body portion of the subject, wherein the second information is representative of the at least one condition of the second external body portion of the subject at approximately the first time, and wherein the second external body portion is normally less exposed to at least one environmental factor than the first external body portion;

determining a difference between the first information and the second information so as to enable an analysis taking into account impact of the at least one environmental factor;

obtaining third information, wherein the third information is representative of the at least one condition of the first external body portion of the subject at approximately a second time;

obtaining fourth information, wherein the fourth information is representative of the at least one condition of the second external body portion of the subject at approximately the second time, wherein the second time occurs at least a period of time after the first time; and determining a difference between the third information and the fourth information.

57. The method of claim 56, further comprising comparing the difference between the first information and the second information with the difference between the third information and the fourth information so as to enable an analysis taking into account impact of the at least one environmental factor over at least the period of time.

58. The method of claim 57, further comprising enabling the subject to receive an indication of the impact of the at least one environmental factor over at least the period of time.

59. A method of enabling an analysis taking into account exposure of at least one external body portion to the environment, the method comprising:

obtaining first information representative of at least one condition of a first external body portion of a subject, wherein the first information is representative of the at least one condition of the first external body portion of the subject at approximately a first time;

obtaining second information representative of at least one condition of a second external body portion of the subject, wherein the second information is representative of the at least one condition of the second external body portion of the subject at approximately the first time, and wherein the second external body portion is normally less exposed to at least one environmental factor than the first external body portion;

determining a difference between the first information and the second information so as to enable an analysis taking into account impact of the at least one environmental factor;

obtaining third information, wherein the third information is representative of the at least one condition of the first external body portion of the subject at approximately a second time;

obtaining fourth information, wherein the fourth information is representative of the at least one condition of the second external body portion of the subject at approximately the second time, wherein the second time occurs at least a period of time after a treatment of the first external body portion is initiated; and determining a difference between the third information and the fourth information.

60. The method of claim 59, further comprising comparing the difference between the first information and the second information with the difference between the third information and the fourth information so as to enable a determination of at least initial effectiveness of the treatment.

61. The method of claim 60, further comprising enabling the subject to receive an indication of the at least initial effectiveness of the treatment.

62. A method of determining at least initial effectiveness of a treatment, the method comprising:

obtaining first information representative of at least one condition of a first external body portion of a subject;

obtaining second information representative of at least one condition of a second external body portion of the subject;

determining a difference between the first information and the second information;

obtaining third information, wherein the third information is representative of the at least one condition of the first external body portion at least a period of time after a treatment of the first external body portion is initiated;

determining a difference between the third information and the second information; and comparing the difference between the first information and the second information with the difference between the third information and the second information so as to enable a determination of at least the initial effectiveness of the treatment of the first external body portion.

63. The method of claim 62, further comprising enabling the subject to receive an indication of the at least initial effectiveness of the treatment.

64. The method of claim 62, further comprising enabling the subject to receive an indication of at least one of the difference between the first information and the second information and the difference between the third information and the second information.

65. The method of claim 64, further comprising sending the indication to the subject via at least one of a package delivery service and a computer network.

66. The method of claim 64, wherein the indication comprises a graphic illustration.

67. The method of claim 62, wherein the second external body portion is normally less exposed to at least one environmental factor than the first external body portion.

68. The method of claim 62, wherein the at least one condition comprises at least one of texture, elasticity, dryness, cellulitis, sweating, aging, wrinkles, exfoliation, desquamation, homogeneity of color, micro-circulation, shininess, softness, smoothness, hydration, sebum production, cleanliness, irritation, redness, vasomotion, vasod ilation, vasoconstriction, pigmentation, and freckles.

69. The method of claim 62, wherein the treatment comprises applying at least one of a cosmetic product and a care product to the first external body portion.

70. The method of claim 69, further comprising enabling the subject to receive information regarding the at least one product.

71. The method of claim 70, wherein the product information is communicated to the subject using at least one of a package delivery service and a computer network.

72. The method of claim 70, further comprising at least one of offering the at least one product for sale to the subject and providing the subject with information enabling the subject to purchase the at least one product.

73. The method of claim 67, wherein the at least one environmental factor is chosen from ultraviolet radiation, extreme temperature, wind, pollution, and shaving.

74. The method of claim 67, further comprising enabling the subject to receive a notification about an impact of the at least one environmental factor.

75. The method of claim 67, wherein the first external body portion comprises skin located on the face of the subject, and the second external body portion comprises one of skin located on the upper buttocks of the subject and skin located on an inner surface of an upper part of at least one of the subject's arms.

76. The method of claim 67, wherein the first external body portion comprises at least one of hair and skin located on the scalp of the subject and the second external body portion comprises at least one of hair and skin located in the pubic area of the subject.

77. The method of claim 67, wherein the first external body portion comprises a fingernail and the second external body portion comprises a toenail.

78. The method of claim 62, wherein the at least one condition represented by the first information is substantially absent from the second external body portion.

79. The method of claim 78, wherein the at least one condition represented by the first information comprises at least one of eczema, psoriasis, acne, and atopic dermatitis.

80. The method of claim 62, wherein the treatment comprises administering at least one pharmaceutical compound to the first external body portion.

81. The method of claim 80, further comprising enabling the subject to receive information regarding the at least one compound.

82. The method of claim 62, further comprising determining a subsequent treatment for the first external body portion, wherein the determining of the subsequent treatment is based on the comparison between the differences.

83. The method of claim 82, further comprising enabling the subject to receive information regarding at least the subsequent treatment.

84. A method of determining at least initial effectiveness of a treatment, the method comprising:
    obtaining first information, wherein the first information is representative of at least one condition of a first external body portion of a subject at approximately a first time;
    obtaining second information, wherein the second information is representative of at least one condition of a second external body portion of the subject at approximately the first time;
    determining a difference between the first information and the second information;
    obtaining third information, wherein the third information is representative of the at least one condition of the first external body portion at approximately a second time;
    obtaining fourth information, wherein the fourth information is representative of the at least one condition of the second external body portion at approximately the second time, wherein the second time occurs at least a period of time after a treatment of the first external body portion is initiated;
    determining a difference between the third information and the fourth information; and
    comparing the difference between the first information and the second information with the difference between the third information and the fourth information so as to enable a determination of at least initial effectiveness of the treatment of the first external body portion.

85. The method of claim 84, further comprising enabling the subject to receive an indication of the at least initial effectiveness of the treatment.

86. The method of claim 84, further comprising enabling the subject to receive an indication of at least one of the difference between the first information and the second information and the difference between the third information and the fourth information.

87. The method of claim 86, further comprising sending the indication to the subject via at least one of a package delivery service and a computer network.

88. The method of claim 86, wherein the indication comprises a graphic illustration.

89. The method of claim 84, wherein the second external body portion is normally less exposed to at least one environmental factor than the first external body portion.

90. The method of claim 84, wherein the at least one condition comprises at least one of texture, elasticity, dryness, cellulitis, sweating, aging, wrinkles, exfoliation, desquamation, homogeneity of color, micro-circulation, shininess, softness, smoothness, hydration, sebum production, cleanliness, irritation, redness, vasomotion, vasod ilation, vasoconstriction, pigmentation, and freckles.

91. The method of claim 84, wherein the treatment comprises applying at least one of a cosmetic product and a care product to the first external body portion.

92. The method of claim 91, further comprising enabling the subject to receive information regarding the at least one product.

93. The method of claim 92, wherein the product information is communicated to the subject using at least one of a package delivery service and a computer network.

94. The method of claim 92, further comprising at least one of offering the at least one product for sale to the subject and providing the subject with information enabling the subject to purchase the at least one product.

95. The method of claim 89, wherein the at least one environmental factor is chosen from ultraviolet radiation, extreme temperature, wind, pollution, and shaving.

96. The method of claim 89, further comprising enabling the subject to receive a notification about an impact of the at least one environmental factor.

97. The method of claim 89, wherein the first external body portion comprises skin located on the face of the subject, and the second external body portion comprises one of skin located on the upper buttocks of the subject and skin located on an inner surface of an upper part of at least one of the subject's arms.

98. The method of claim 89, wherein the first external body portion comprises at least one of hair and skin located on the scalp of the subject and the second external body portion comprises at least one of hair and skin located in the pubic area of the subject.

99. The method of claim 89, wherein the first external body portion comprises a fingernail and the second external body portion comprises a toenail.

100. The method of claim 84, wherein the at least one condition represented by the first information is substantially absent from the second external body portion.

101. The method of claim 100, wherein the at least one condition represented by the first information comprises at least one of eczema, psoriasis, acne, and atopic dermatitis.

102. The method of claim 84, wherein the treatment comprises administering at least one pharmaceutical compound to the first external body portion.

103. The method of claim 102, further comprising enabling the subject to receive information regarding the at least one compound.

104. The method of claim 84, further comprising determining a subsequent treatment for the first external body portion, wherein the determining of the subsequent treatment is based on the comparison between the differences.

105. The method of claim 104, further comprising enabling the subject to receive information regarding at least the subsequent treatment.

106. The method of claim 84, wherein each of the obtaining of the first information, the obtaining of the second information, the obtaining of the third information, and the obtaining of the fourth information comprises acquiring a quantitative measurement of at least one condition.

107. The method of claim 106, wherein the quantitative measurement is chosen from corneometry, dermal torque measurement, pH measurement, colorimetry, sebumetry, lipometry, confocal measurement, epidermal turnover measurement, skin layer thickness measurement, blood microcirculation measurement, desquamation rate measurement, water loss measurement, skin hydration measurement, scoring with a densiscore-type tool, and measurement of sudatory function.

108. The method of claim 106, wherein each of the determining of the difference between the first information and the second information and the determining of the difference between the third information and the fourth information comprises determining at least one difference between quantitative measurements.

109. The method of claim 84, wherein each of the obtaining of the first information, the obtaining of the second information, the obtaining of the third information, and the obtaining of the fourth information comprises acquiring at least one image of a respective external body portion of the subject.

110. The method of claim 109, wherein the at least one image is chosen from photographs, scanned images, ultrasonic images, magnified images, wrinkle projections, and imprints.

111. The method of claim 109, wherein each of the obtaining of the first information, the obtaining of the second information, the obtaining of the third information, and the obtaining of the fourth information further comprises analyzing the at least one image to ascertain at least one of a qualitative property and a quantitative property relating to the at least one condition.

112. The method of claim 111, wherein the analyzing of the at least one image comprises at least one of counting sebaceous glands, counting sweat glands, and visualizing imprints in the at least one image.

113. The method of claim 111, wherein each of the determining of the difference between the first information and the second information and the determining of the difference between the third information and the fourth information comprises determining at least one difference between properties ascertained from analyzing the images.

114. The method of claim 84, wherein each of the obtaining of the first information, the obtaining of the second information, the obtaining of the third information, and the obtaining of the fourth information comprises acquiring at least one external body portion sample.

115. The method of claim 114, wherein the at least one sample is chosen from skin cells, hair cells, fingernail cells, toenail cells, secretions, bioanalytical content, bacteriological content, and enzymatic content.

116. The method of claim 114, wherein the acquiring of the at least one sample is carried out using a technique chosen from adhesive collection absorption, and abrasion.

117. The method of claim 114, wherein each of the obtaining of the first information, the obtaining of the second information, the obtaining of the third information, and the obtaining of the fourth information further comprises analyzing the at least one sample to ascertain at least one of a qualitative property and a quantitative property relating to the at least one condition.

118. The method of claim 117, wherein the qualitative property relates to one of presence and absence of at least one component, and the quantitative property relates to relative quantity of at least one component in the sample.

119. The method of claim 117, wherein the analyzing of the at least one sample is carried out using at least one of an optical, chemical, and biological analysis technique.

120. The method of claim 119, wherein the analysis technique is chosen from gas chromatography/mass spectrometry, gas chromatography/mass spectrometry/mass spectrometry, liquid chromatography/mass spectrometry, liquid chromatography/mass spectrometry/mass spectrometry, ultraviolet observation, fluorescence observation, infrared observation, Raman spectrophotometric observation, and X-ray observation.

121. The method of claim 117, wherein each of the determining of the difference between the first information and the second information and the determining of the difference between the third information and the fourth information comprises determining at least one difference between properties ascertained from analyzing the samples.

122. The method of claim 84, wherein each of the obtaining of the first information, the obtaining of the second information, the obtaining of the third information, and the obtaining of the fourth information comprises receiving information chosen from a quantitative measurement of the at least one condition, at least one external body portion image, and at least one external body portion sample.

123. The method of claim 122, wherein each of the obtaining of the first information, the obtaining of the second information, the obtaining of the third information, and the obtaining of the fourth information further comprises at least one of analyzing the at least one image to ascertain at least one of a qualitative property and a quantitative property relating to the at least one condition and analyzing the at least one sample to ascertain at least one of a qualitative property and a quantitative property relating to the at least one condition.

124. The method of claim 122, wherein the information is received via at least one of a package delivery service and a computer network.

125. The method of claim 84, further comprising:
maintaining a database containing external body portion information for a plurality of subjects; and
conducting an analysis based on a comparison between information in the database and at least one of the first information, the second information, the determined difference between the first information and the second information, the third information, the fourth information, and the difference between the third information and the fourth information.

126. The method of claim 125, further comprising storing at least one of the first information, the second information, the determined difference between the first information and the second information, the third information, the fourth information, and the difference between the third information and the fourth information in the database.

127. The method of claim 84, further comprising:
maintaining a subject record; and
causing storage in the subject record of at least one of the first information, the second information, the determined difference between the first information and the second information, the third information, the fourth information, and the difference between the third information and the fourth information.

128. The method of claim 127, comprising causing storage in the subject record of subject information acquired subsequent to the third information and the fourth information.

129. The method of claim 127, further comprising enabling the subject to access at least a portion of information stored in the subject record.

130. The method of claim 129, further comprising enabling the subject to access the information via at least one of a package delivery service and a computer network.

131. The method of claim 129, further comprising enabling the subject to graphically display the information.

* * * * *